United States Patent [19]
St. Goar et al.

[11] Patent Number: 6,090,096
[45] Date of Patent: *Jul. 18, 2000

[54] ANTEGRADE CARDIOPLEGIA CATHETER AND METHOD

[75] Inventors: Frederick G. St. Goar, Menlo Park; John H. Stevens, Palo Alto; Hanson S. Gifford, III, Woodside, all of Calif.; Bartley P. Griffith, Pittsburgh, Pa.

[73] Assignee: Heartport, Inc., Redwood City, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/839,189

[22] Filed: Apr. 23, 1997

[51] Int. Cl.$^7$ ..................................................... A61M 31/00

[52] U.S. Cl. ........................... 604/509; 604/96; 604/102; 600/18

[58] Field of Search ..................................... 606/159, 192, 606/194; 604/96–102; 600/18

[56] References Cited

U.S. PATENT DOCUMENTS

| | | | |
|---|---|---|---|
| Re. 35,352 | 10/1996 | Peters | 604/4 |
| 3,547,119 | 12/1970 | Hall . | |
| 3,671,979 | 6/1972 | Moulopoulos . | |
| 3,769,960 | 11/1973 | Robinson . | |
| 3,788,328 | 1/1974 | Alley et al. . | |
| 3,833,003 | 9/1974 | Taricco . | |
| 3,851,647 | 12/1974 | Monestere, Jr. . | |
| 3,903,895 | 9/1975 | Alley et al. . | |

(List continued on next page.)

FOREIGN PATENT DOCUMENTS

| | | |
|---|---|---|
| 0218275 A1 | 4/1987 | European Pat. Off. . |
| 0414350 A1 | 6/1990 | European Pat. Off. . |
| 0350302 | 2/1991 | European Pat. Off. . |
| 91/01689 | 2/1991 | WIPO . |
| 91/17720 | 11/1991 | WIPO . |
| 92/17118 | 10/1992 | WIPO . |

OTHER PUBLICATIONS

Black, et al., "The Use of Foley balloon catheters in cardiac surgery," *Eur J. Cardio–thorac Surg.* (1993), 7:617–691.

Andersen et al., "Transluminal Implantation of Artificial Heart Valves . . . " *European Heart Journal,* 1992;13:704–708.

Baxter Healthcare Corporation, "Fogarty Occlusion Catheter: Instructions for Use," ©1994.

Buckberg, "Strategies and Logic of Cardioplegic Delivery to Prevent, Avoid, and Reve rse Ischemic and Reperfusion Damage," *J Thorac Cardio Vasc Surg,* 1987;93:127–129.

Cosgrove, "Management of the Calcified Aorta: An Alternative Method of Occulsion," *Ann Thorac Surg,* 1983;36:718–719.

Crooke et al., "Biventricular Distribution of Cold Blood Cardioplegic Solution Administered by Different Retrograde Techniques," *J Cardiac Thorac Surg,* 1991;102(4):631–636.

Datascope FDA 510(k) Application, "Percluder—DL Occluding Balloon," Oct. 12, 1993.

DLP Medtronic Alternative Access Cannulae Brochure, ©1995.

DLP, Inc., Directions for Use: Cardioplegic Pressure Cannula with Vent Line, Code #14009 9 Gauge (no date).

Erath et al., "Balloon Catheter Occulsion of the Ascending Aorta," *Ann Thorac Surg,* 1983;35:560–561.

*Primary Examiner*—Wynn Wood Coggins
*Assistant Examiner*—Deborah Blyveis
*Attorney, Agent, or Firm*—Jens E. Hoekendijk; Jeffry J. Grainger

[57] ABSTRACT

A cardioplegia catheter is configured to extend into the ascending aorta with a proximal portion of the shaft extending into a left chamber of the heart through the aortic valve and out of the heart through a penetration in a wall thereof. The cardioplegia catheter has an occlusion member configured to occlude the ascending aorta between the brachiocephalic artery and the coronary ostia. An arterial return cannula delivers oxygenated blood to the arterial system downstream of the occlusion member, while cardioplegic fluid is delivered through a lumen in the cardioplegia catheter upstream of the occlusion member to induce cardioplegic arrest.

11 Claims, 13 Drawing Sheets

U.S. PATENT DOCUMENTS

| | | |
|---|---|---|
| 4,000,739 | 1/1977 | Stevens . |
| 4,056,854 | 11/1977 | Boretos et al. . |
| 4,073,297 | 2/1978 | Kopp . |
| 4,122,858 | 10/1978 | Schiff . |
| 4,173,981 | 11/1979 | Mortensen et al. . |
| 4,248,224 | 2/1981 | Jones . |
| 4,276,874 | 7/1981 | Wolvek et al. . |
| 4,285,341 | 8/1981 | Pollack . |
| 4,287,892 | 9/1981 | Schiff . |
| 4,289,129 | 9/1981 | Turner . |
| 4,310,017 | 1/1982 | Raines . |
| 4,327,709 | 5/1982 | Hanson et al. . |
| 4,430,081 | 2/1984 | Timmermans . |
| 4,527,549 | 7/1985 | Gabbay . |
| 4,531,935 | 7/1985 | Berryessa . |
| 4,531,936 | 7/1985 | Gordon . |
| 4,540,399 | 9/1985 | Litzie et al. . |
| 4,592,340 | 6/1986 | Boyles . |
| 4,596,552 | 6/1986 | DeVries . |
| 4,601,713 | 7/1986 | Fuqua . |
| 4,639,252 | 1/1987 | Kelly et al. . |
| 4,664,125 | 5/1987 | Pinto . |
| 4,697,574 | 10/1987 | Karcher et al. . |
| 4,704,102 | 11/1987 | Guthery . |
| 4,705,507 | 11/1987 | Boyles . |
| 4,722,732 | 2/1988 | Martin . |
| 4,723,550 | 2/1988 | Bales et al. . |
| 4,741,328 | 5/1988 | Gabbay . |
| 4,751,924 | 6/1988 | Hammerschmidt et al. . |
| 4,770,652 | 9/1988 | Mahurkar . |
| 4,771,777 | 9/1988 | Horzewski et al. . |
| 4,785,795 | 11/1988 | Singh . |
| 4,790,825 | 12/1988 | Bernstein et al. . |
| 4,804,365 | 2/1989 | Litzie et al. . |
| 4,877,035 | 10/1989 | Bogen et al. . |
| 4,886,507 | 12/1989 | Patton et al. . |
| 4,889,137 | 12/1989 | Kolobow . |
| 4,902,272 | 2/1990 | Milder et al. . |
| 4,902,273 | 2/1990 | Choy et al. . |
| 4,909,258 | 3/1990 | Kuntz et al. ............................ 128/658 |
| 4,943,275 | 7/1990 | Stricker . |
| 4,960,412 | 10/1990 | Fink . |
| 5,009,636 | 4/1991 | Wortley et al. . |
| 5,011,469 | 4/1991 | Buckberg et al. . |
| 5,013,296 | 5/1991 | Buckberg et al. . |
| 5,024,668 | 6/1991 | Peters et al. . |
| 5,041,098 | 8/1991 | Loiterman et al. . |
| 5,069,661 | 12/1991 | Trudell . |
| 5,073,168 | 12/1991 | Danforth . |
| 5,088,984 | 2/1992 | Fields . |
| 5,106,368 | 4/1992 | Uldall et al. . |
| 5,116,305 | 5/1992 | Milder et al. . |
| 5,125,903 | 6/1992 | McLaughlin et al. . |
| 5,167,628 | 12/1992 | Boyles . |
| 5,171,232 | 12/1992 | Castillo et al. . |
| 5,176,619 | 1/1993 | Segalowitz . |
| 5,186,713 | 2/1993 | Raible . |
| 5,195,942 | 3/1993 | Weil et al. . |
| 5,219,326 | 6/1993 | Hattler . |
| 5,226,427 | 7/1993 | Buckbert et al. . |
| 5,250,038 | 10/1993 | Melker et al. . |
| 5,254,097 | 10/1993 | Schock et al. . |
| 5,270,005 | 12/1993 | Raible . |
| 5,308,320 | 5/1994 | Safar et al. . |
| 5,312,344 | 5/1994 | Grinfeld et al. . |
| 5,322,509 | 6/1994 | Rickerd . |
| 5,330,451 | 7/1994 | Gabbay . |
| 5,334,142 | 8/1994 | Paradis . |
| 5,370,640 | 12/1994 | Kolff . |
| 5,374,245 | 12/1994 | Mahurkar . |
| 5,382,239 | 1/1995 | Orr et al. . |
| 5,411,027 | 5/1995 | Wiklund et al. . |
| 5,421,825 | 6/1995 | Farcot . |
| 5,425,708 | 6/1995 | Nasu . |
| 5,433,700 | 7/1995 | Peters . |
| 5,451,207 | 9/1995 | Yock . |
| 5,452,733 | 9/1995 | Sterman et al. . |
| 5,458,574 | 10/1995 | Machold et al. . |
| 5,478,309 | 12/1995 | Sweezer et al. . |
| 5,487,730 | 1/1996 | Marcadis et al. . |
| 5,499,996 | 3/1996 | Hill . |
| 5,505,698 | 4/1996 | Booth et al. . |
| 5,522,800 | 6/1996 | Crocker ...................................... 604/96 |
| 5,527,292 | 6/1996 | Adams et al. . |
| 5,545,214 | 8/1996 | Stevens . |
| 5,571,215 | 11/1996 | Sterman et al. . |
| 5,584,803 | 12/1996 | Stevens et al. . |
| 5,597,377 | 1/1997 | Aldea . |
| 5,599,329 | 2/1997 | Gabbay ................................... 604/284 |
| 5,682,906 | 11/1997 | Sterman et al. . |
| 5,688,245 | 11/1997 | Runge . |
| 5,695,457 | 12/1997 | St. Goar et al. . |
| 5,755,687 | 5/1998 | Donlon . |
| 5,765,568 | 6/1998 | Sweezer, Jr. et al. ................... 128/898 |

OTHER PUBLICATIONS

Foster et al., "Proximal Control of Aorta with a Balloon Catheter," *Surg, Gynecological & Obstetrics,* 1971;693–694.

Gundry et al, "A Comparison of Retrograde of Cardioplegia Versus Antegrade Cardioplegia in the Presence of Coronary Artery Obstruction," *Ann Thorac Surg,* 1984;38(2):124–127.

Ishizaka, "Myocardial Protection by Retrograde Cardiac Perfusion with Cold Modified Krebs Solution through Coronary Sinus During Complete Ischemic Arrest for 120 Minutes," *J Jpn Assn Thorac Surg,* 1982;30(3):306–318.

Leggett et al., "Fiberoptic Cardioscopy Under Cardiopulmonary Bypass: Potential for Cardioscopic Surgery?" *Ann Thorac Surg* 1994;58:222–225.

Lust et al., "Improved Protection of Chronicaly Inflow–limited Myocardium with Retrograde Coronary Sinus Cardioplegia," *Circulation III,* 1988;78(5):217–223.

Medex, Inc., from 1990 Product Catalog.

Medex, Inc., MX220 Single Tuohy–Borst Adaptor: Instructions for Use, 1992.

Meditech, Boston Scientific Corporation, "Occlusion Balloon Catheters: Instructions for Use,"+Rev. Mar. 1991.

Medtronic Bio–Medicus, Inc., "Bio–Medicus Cannula Introducer Instructions for Use Manual," PN 85146–Rev. C (Jul. 1991).

Medtronic Bio–Medicus, Inc., "Bio–Medicus Cannula Instructions for Use Manual, Sterile and Non–Pyrogenic Single–Use Only," PN 85281 Rev C (Oct. 1991).

Medtronic Bio–Medicus Femoral Cannulae advertisement, ©1991.

Medtronic Bio–Medicus Pediatric Cannulae advertisement, ©1991.

Medtronic Bio–Medicus Percutaneous Cannula Kits advertisement, ©1991.

Ogawa, "Aortic Arch Reconstruction Without Aortic Cross–clamping Using Separate Extracorporeal Circulation," *J Jpn Assn Thorac Surg,* 1993;2185–2190.

Okita et al., "Utilization of Triple–Lumen Balloon Catheter for Occlusion of the Ascending Aorta During Distal Aortic Arch Surgery with Hypothermic Retrograde Cerebral Circulation Technique through Left Thoractotomy," *Journal of Cardiac Surgery,* 1996;10:699–702.

Peters, "The Promise of Cardioscopy Surgery," *AustalAs J Cardiac Thorac Surg,* 1993;2(3):152–154.

Pilling Surgical Instruments, Vascular Clamps– Cooley brochure, p. 385 (no date).

Razi, "The Challenge of Calcific Aortitis," *J Cardiac Thorac Surg,* 1993;8:102–107.

Research Medical, Inc., Cardioplegia Products, Product Catalog 1995.

Research Medical, Inc., Fem–Flex II Femoral Percutaneous Cannulae advertisement, *Ann Thorac Surg,* Jan. 1995, p. A38.

Rossi, "Long–term Cardiopulmonary Bypass by Peripheral Cannulation in a Model of Total Heart Failure," *J Thorac Cardio Vasc Surg,* 1990;100:914–921.

Sabiston, *Textbook of Surgery,* $10^{th}$ Ed., 1972;2021–2023, 2114–2121.

Sakaguchi et al., "Aortic Valve Replacement and Coronary Artery Bypass," *J Jpn Assoc for Thorac Surg,* 1993;41(6):1063–1068.

Uchida et al., "Percutaneous Cardiomyotomy and Valvulotomy with Angioscopic Guidance," *American Heart Journal,* 121(4, part 1):1221–1224.

Uchida et al., "Percutaneous Fiberoptic Angioscopy of the Cardiac Valves," *American Heart Journal,* 1991;121(6 part 1):1791–1798.

Yamaguchi, "A Case of Reoperation Using a Balloon Catheter with Blocked Pars Ascendes Aortae," *Kyobu Geka,* 1991;42(11):961–964.-

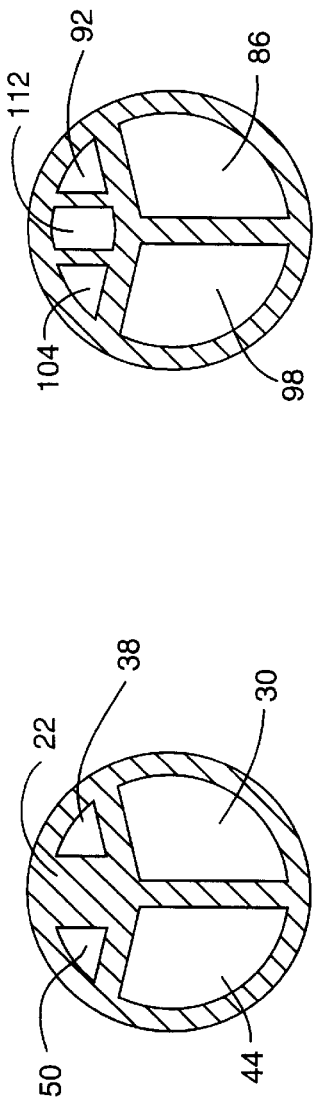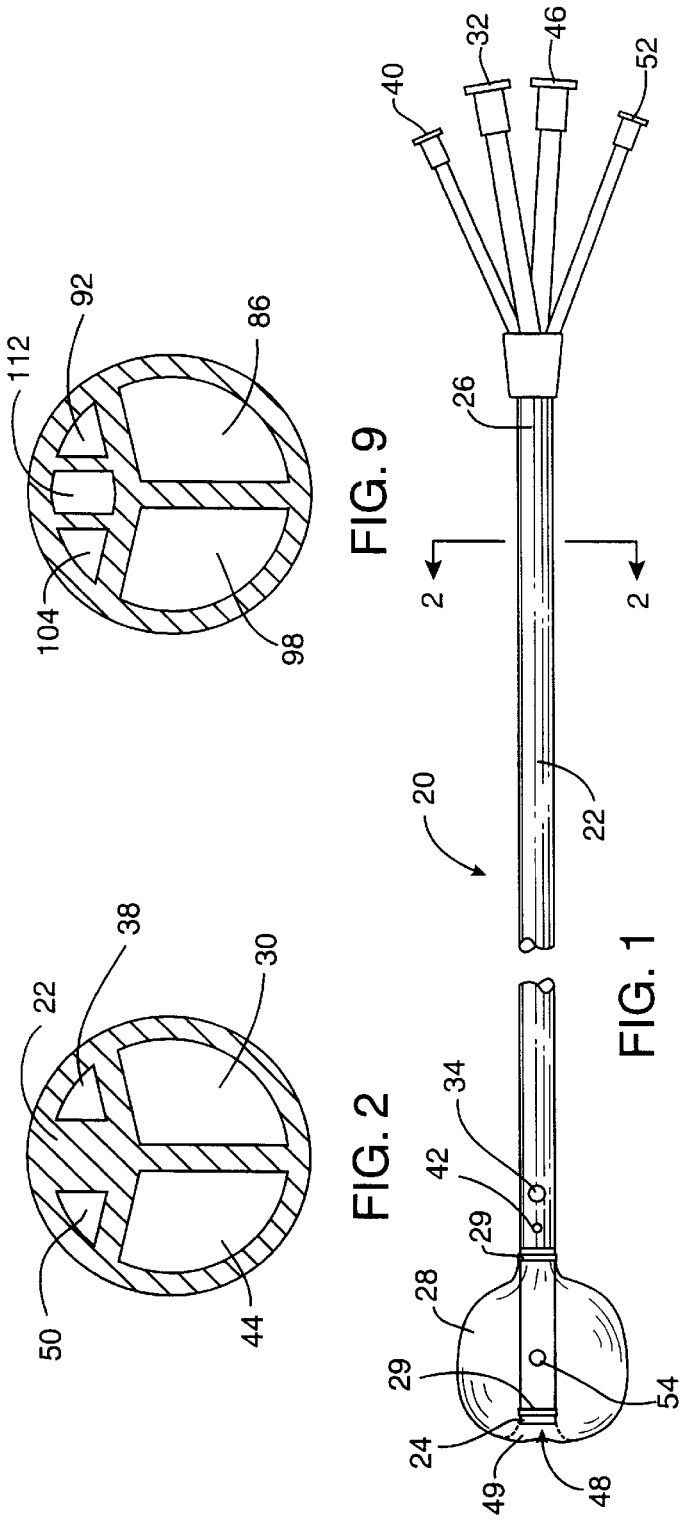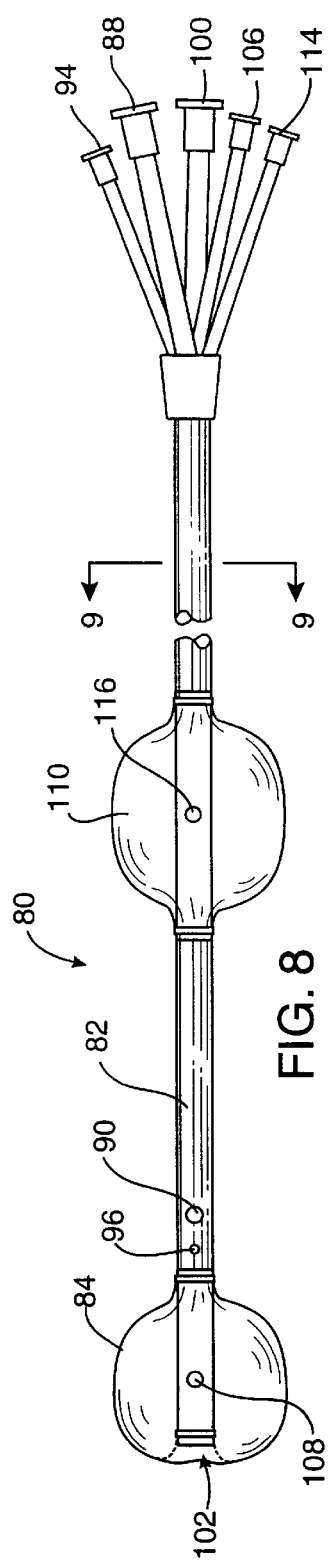

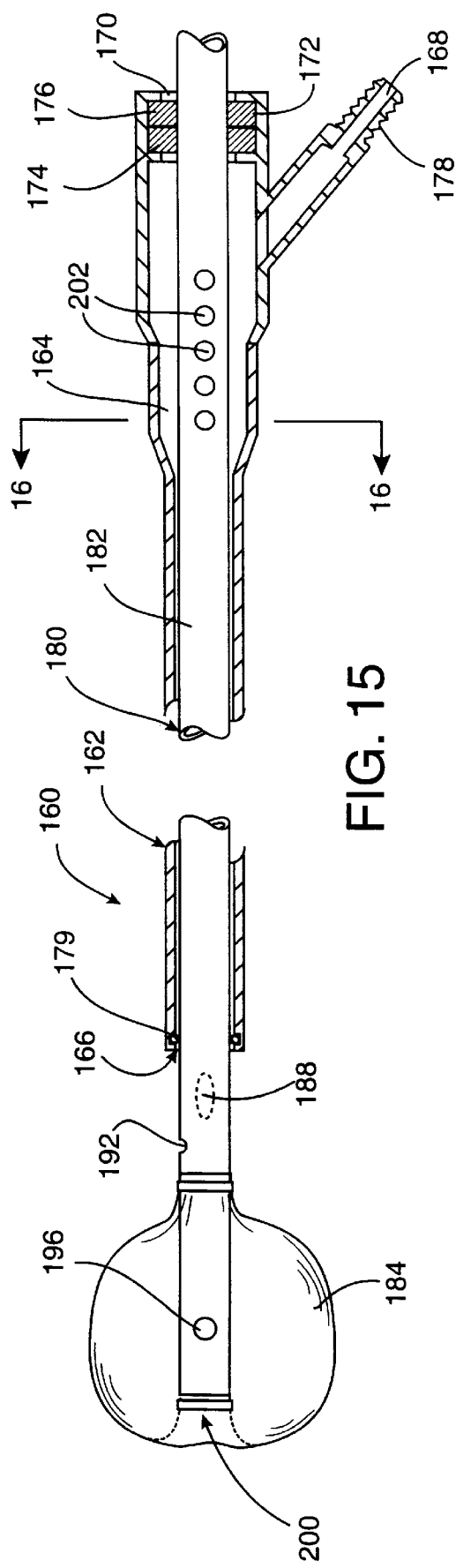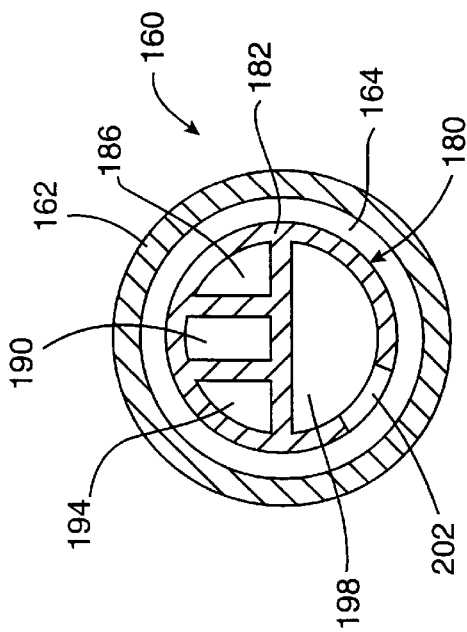
FIG. 15
FIG. 16

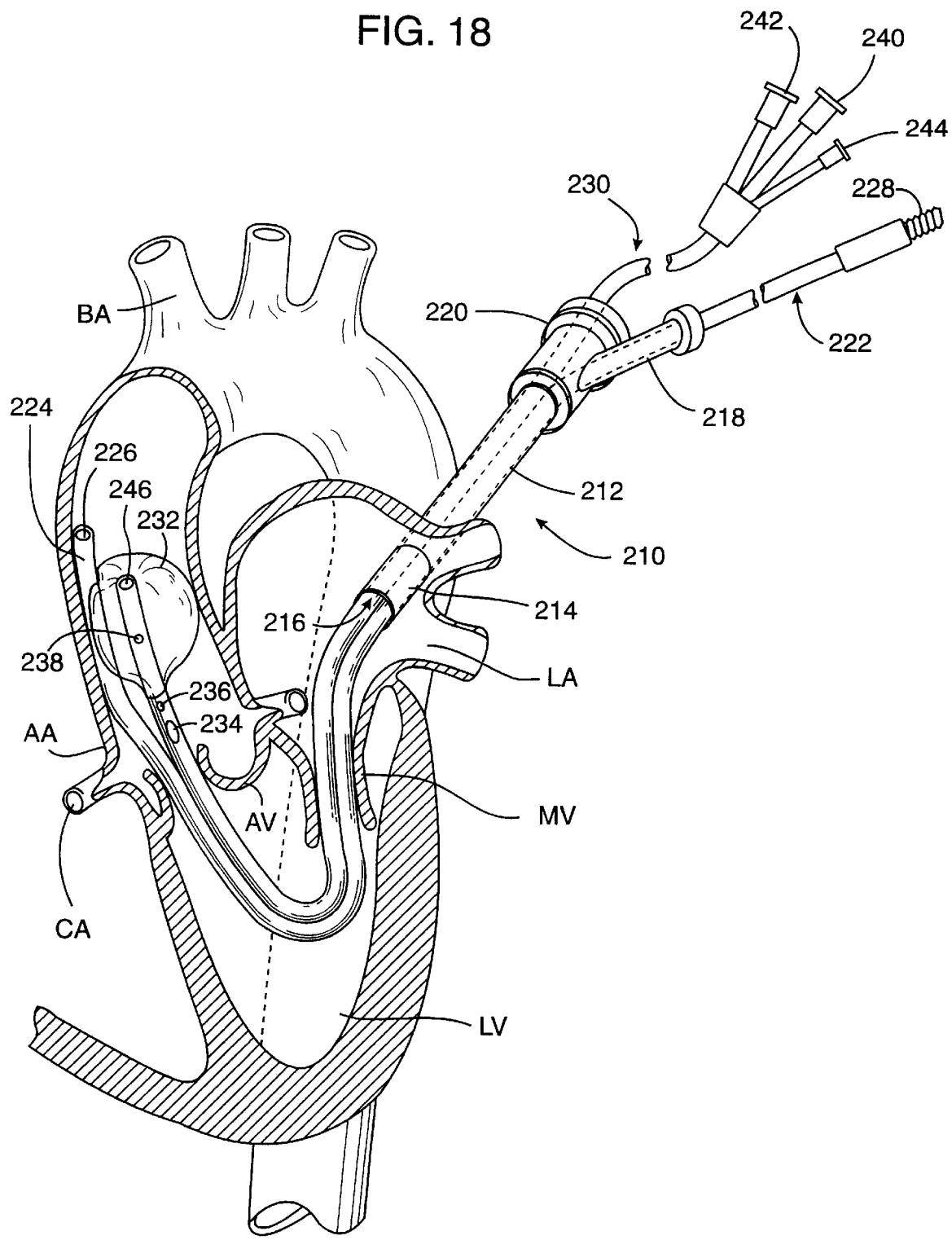

ANTEGRADE CARDIOPLEGIA CATHETER AND METHOD

FIELD OF THE INVENTION

This invention relates generally to catheters for use in medical procedures, and more specifically to a catheter system for inducing cardioplegic arrest and maintaining circulation of blood.

BACKGROUND OF THE INVENTION

Cardiac surgery is conventionally performed with the patient's heart stopped and with circulation of blood maintained by extracorporeal cardiopulmonary bypass, a state known as cardioplegic arrest. Cardioplegic arrest conventionally requires the creation of a large incision in the chest, known as a sternotomy or thoracotomy, to expose the heart and great vessels of the thorax. Through this large incision, a steel clamp, called a cross-clamp, is placed around the aorta between the coronary arteries, which deliver blood to the heart muscle, and the brachiocephalic artery, which delivers blood to the head and neck. The clamp is closed so as to collapse the aorta, thereby partitioning the heart and coronary circulation from the remainder of the arterial system downstream of the cross-clamp. Pharmaceutical agents may then be delivered into the coronary arteries or aorta upstream of the cross-clamp so as to arrest cardiac function. Circulation of blood is maintained throughout the body by placing a venous drainage cannula in a major vein or in the right side of the heart to withdraw venous blood, routing the blood to an extracorporeal oxygenator, and pumping the blood back into the arterial system through a cannula positioned in a major artery, typically in the aorta just downstream of the cross-clamp.

While cardiopulmonary bypass with cardioplegic arrest is currently the gold standard for performing most cardiac surgical procedures, conventional techniques suffer from several drawbacks. Important among these are the high degree of pain and trauma, risk of complications and long recovery time which result from median sternotomy and other types of gross thoracotomy. Furthermore, the use of a cross-clamp on a calcified or otherwise diseased aorta can produce serious complications such as embolization of plaque, potentially leading to stroke and other neurological problems.

In U.S. Pat. No. Reissue Re35,352 to Peters, which is assigned to the assignee of the present invention and is hereby incorporated herein by reference, it is suggested that the use of a cross-clamp to achieve cardioplegic arrest could be avoided through the use of an endovascular balloon occlusion catheter positioned from a femoral artery into the ascending aorta. A balloon at the distal tip of the occlusion catheter can be expanded to occlude the aorta between the coronary arteries and brachiocephalic artery, and cardioplegic fluid then delivered through a lumen in the catheter into the aorta upstream of the balloon so as to arrest the heart. Cardiopulmonary bypass is established by placing arterial and venous cannulae in a femoral artery and femoral vein, respectfully, and routing the patient's blood through an extracorporeal oxygenator and pump.

While the endovascular technique proposed in the Peters patent is useful in many cardiac surgeries to avoid the need for median sternotomy and aortic cross-clamping, the technique can have disadvantages in some situations. For example, in patients with severe peripheral vascular disease, the balloon occlusion catheter may be difficult to introduce into the femoral arteries and to advance transluminally into the ascending aorta.

Another technique for inducing cardioplegic arrest without the use an aortic cross-clamp is proposed in U.S. Pat. No. 5,312,344 to Grinfeld. This technique involves the placement of a balloon occlusion catheter into the ascending aorta directly through a puncture in the aortic wall. The balloon occlusion catheter has an occlusion balloon at its distal tip which is used to occlude the aorta between the coronaries and the brachiocephalic artery. The catheter further includes an arterial return lumen through which blood may be delivered into the aorta downstream of the balloon, eliminating the need for a separate arterial return cannula.

The Grinfeld technique, however, also suffers from a variety of disadvantages. First, because the catheter is introduced through the ascending aortic wall, the technique requires dissection and retraction of the various tissues surrounding the ascending aorta to expose the vessel. This is particularly difficult if the procedure is to be performed minimally-invasively through trocars or small incisions, without a median sternotomy or other gross thoracotomy. In addition, many patients who receive cardiac surgery have some degree of aortic calcification or other aortic disease. In such patients, it is undesirable to puncture the aortic wall with a catheter as taught by Grinfeld, as this could embolize plaque, initiate or aggravate an aortic dissection, or create other problems. Finally, in Grinfeld's technique, because oxygenated blood is returned to the arterial system through a lumen within the aortic occlusion catheter itself, should the surgeon desire to remove the occlusion balloon from the aorta due to a balloon puncture or other problem, the patient must first be rewarmed and weaned from extracorporeal cardiopulmonary bypass before the balloon can be removed, lengthening the procedure considerably.

What is needed therefore, are devices and methods for inducing cardioplegic arrest and maintaining circulation of oxygenated blood which do not require median sternotomy or other gross thoracotomy and which eliminate the need for aortic cross-clamping, but which overcome the disadvantages of known endovascular balloon occlusion devices. The devices and methods should be useful in patients having severe peripheral vascular disease as well as in those having aortic calcification, without creating a high risk of embolization, aortic dissection, or other complications. The devices and methods should further avoid the need to directly access the aorta and the associated need to dissect and retract the surrounding tissues. Moreover, the devices and methods should optionally allow occlusion of the aorta to be discontinued and any occlusion device to be removed from and replaced in the aorta without weaning the patient from cardiopulmonary bypass.

SUMMARY OF THE INVENTION

The invention provides catheter systems and methods for inducing cardioplegic arrest that overcome many of the disadvantages of known techniques. The systems and methods of the invention facilitate endovascular occlusion of the ascending aorta, delivery of cardioplegic fluid, venting the aortic root, monitoring of aortic root pressure, and circulation of oxygenated blood through the patient's arterial system without the need for median sternotomy, aortic cross-clamping, or direct access to or puncture of the aorta. If peripheral vascular disease makes endovascular access through peripheral vessels difficult, the systems and methods of the invention may be utilized without such access. Optionally, the systems and methods of the invention further allow aortic occlusion to be discontinued and occlusion devices to be removed from the aorta without weaning the patient from cardiopulmonary bypass.

In a first embodiment, the invention provides a cardioplegia catheter for inducing cardioplegic arrest that comprises a shaft with a distal end, a proximal end, an opening near the distal end, a port at the proximal end, and an inner lumen fluidly connecting the port and the opening. A distal portion of the shaft is configured to extend into the ascending aorta with a proximal portion of the shaft extending into a left chamber of the heart through the aortic valve and out of the heart through a penetration in a wall thereof. An occlusion member is mounted to the shaft distally of the opening and configured to occlude the ascending aorta between the brachiocephalic artery and the coronary ostia. In a preferred embodiment, the cardioplegia catheter is configured to be introduced through the wall of the heart into the left atrium, from which it is advanced through the mitral valve into the left ventricle, and through the aortic valve into the ascending aorta. The shaft is long enough to extend out of the heart and out of the chest when the distal end is positioned in the ascending aorta, preferably being about 25–75 cm in length.

The occlusion member is preferably a balloon, and an inflation lumen extends through the shaft in communication with the interior of the balloon for delivering an inflation fluid into the balloon. The occlusion member may alternatively be a collapsible one-way valve with one or more movable leaflets, an umbrella-like expanding membrane, or other mechanical occlusion device.

The cardioplegia catheter of the invention may further include a sealing device for sealing the penetration in the wall of the heart around the shaft to inhibit blood flow therethrough. The sealing device preferably comprises a purse string suture that may be applied to the wall of the heart around the penetration. The purse string suture may then be tensioned to seal the penetration around the catheter shaft.

In order to facilitate positioning the distal end of the cardioplegia catheter in the ascending aorta from a left chamber of the heart, a distal portion of the catheter may be preshaped in an appropriate shape that the catheter naturally assumes in an unbiased, unrestrained condition. For embodiments positioned via the left atrium, the shaft may be preshaped such that the distal end is maneuverable around the sharp turn from the mitral valve toward the aortic valve. In such a shape, a distal portion of the catheter shaft is preferably disposed at an angle between about 20 and 90 degrees relative to a proximal portion of the shaft. In order to facilitate introduction of a cardioplegia catheter having such a shape, a relatively stiff obturator may be placed in an inner lumen of the catheter to straighten the shaft during introduction, the obturator being withdrawn from the catheter as it is advanced into the aorta.

As an alternative or supplement to a preshaped shaft, the invention further provides a guiding device for guiding the distal end of the shaft into the ascending aorta. In one embodiment, the guiding device comprises a guidewire positionable in the ascending aorta from the left chamber of the heart. In another embodiment, the guiding device comprises a stylet removably positionable in a lumen within the shaft, the stylet having an end portion for shaping the shaft. The stylet may have a shaping mechanism for shaping the end portion, whereby an actuator at a proximal end of the stylet may be actuated so as to cause the stylet to assume a suitable shape, thereby imparting the shape to the cardioplegia catheter. The shaping mechanism may comprise steering wires, push rods, or other mechanisms suitable for changing the shape of the stylet.

In a further embodiment the guiding device comprises a flow directed catheter positionable through a lumen in the shaft and having an expandable member at its distal end configured to be carried by blood flow into the ascending aorta. Once the flow-directed catheter has been positioned in the ascending aorta, the cardioplegia catheter may be slidably positioned over the flow-directed catheter. Alternatively, the flow directed catheter may have an inner lumen through which a guidewire is first positioned into the ascending aorta, the flow-directed catheter then being withdrawn and the cardioplegia catheter positioned over the guidewire into the ascending aorta. A source of cardioplegic fluid is usually connected in communication with the port at the proximal end of the shaft, allowing cardioplegic fluid to be delivered through the inner lumen into the ascending aorta upstream of the occlusion member to arrest the heart. Preferably, the inner lumen is configured to deliver a cardioplegic fluid containing blood at a rate of at least 150 ml/min and a pressure less than about 350 mmHg, the inner lumen having a cross-sectional area of at least about 2.2 mm$^2$ between the port and the opening.

Arterial blood circulation may be maintained in various ways. In one embodiment, the cardioplegia catheter includes a delivery opening distal to the occlusion member, a delivery port at the proximal end of the shaft, and a delivery lumen extending between the delivery port and the delivery opening. The delivery lumen may be configured to provide return of oxygenated blood to the aorta downstream of the occlusion member as a substitute for or a supplement to a separate arterial return cannula. As the sole conduit for return of blood to a patient under full cardiopulmonary bypass the delivery lumen is configured to deliver blood at a rate of at least about 4 liters/min at a pressure no more than about 350 mmHg, usually having a cross-sectional area of at least about 30 mm$^2$.

In alternative embodiments, return of arterial blood may be provided by one or more arterial cannulae positioned independently of the cardioplegia catheter. In one embodiment, an arterial return cannula is slidably positioned through the delivery lumen in the cardioplegia catheter, allowing the arterial return cannula to be placed in any of various positions relative to the occlusion member, and allowing the occlusion member to be withdrawn from the aorta without removing the arterial return cannula. In another embodiment, the arterial cannula is placed in parallel with the cardioplegia catheter through the left atrium, left ventricle and aortic valve, and the cardioplegic catheter has an occlusion member that conforms around the cardioplegia cannula to occlude the ascending aorta. Alternatively, the arterial return cannula may have a lumen configured to allow the cardioplegia catheter to be slidably positioned through it. The cardioplegia catheter has a blood return lumen extending distally of the occlusion member and at least one inlet port in its sidewall through which blood may enter the blood return lumen from the arterial return cannula. In alternative embodiments, an arterial return cannula is placed in a peripheral vessel selected from the femoral, iliac, subclavian or axillary artery. In a particular embodiment, the arterial cannula is configured to extend into or near the aortic arch from the peripheral artery, allowing arterial blood to be returned such that flow through the aorta and its branches is in an antegrade direction.

The cardioplegia catheter of the invention preferably includes a pressure monitoring device coupled to the shaft for monitoring pressure in the ascending aorta proximal to the occlusion member. Usually, a pressure opening is provided in the shaft proximal to the occlusion member, a pressure port is disposed at the proximal end of the shaft, and a pressure lumen extends between the pressure port and the pressure opening. A pressure monitoring device may be coupled to the pressure port at the proximal end of the shaft so as to measure pressure in the aortic root during the procedure.

A method of inducing cardioplegic arrest according to the invention comprises the steps of: forming a penetration in a wall of a left chamber of the heart; positioning a cardioplegia catheter through the penetration into the left chamber of the heart; forming a seal between the wall of the heart and the cardioplegia catheter to inhibit leakage of blood through the penetration; advancing a distal end of the cardioplegia catheter in the direction of blood flow from the left chamber of the heart, through the aortic valve and into the ascending aorta; expanding an occlusion member on the cardioplegia catheter so as to occlude the ascending aorta downstream of the coronary ostia and upstream of the brachiocephalic artery; delivering cardioplegic fluid through the coronary vasculature to the myocardium so as to arrest cardiac function; and circulating oxygenated blood in the patient's arterial system downstream of the occlusion member.

In a preferred embodiment, the step of circulating comprises positioning an arterial cannula in an arterial location downstream of the occlusion member, the arterial cannula being independently positionable relative to the occlusion member. The arterial cannula is usually positioned in a peripheral artery selected from a femoral artery, iliac artery, subclavian artery or axillary artery. The the step of sealing preferably comprises placing a purse string suture in the wall of the heart around the penetration.

The step of advancing preferably comprises sliding the cardioplegia catheter over a guiding device positioned in the left chamber of the heart and extending into the ascending aorta. The guiding device may comprise a guidewire, flow-directed catheter, stylet, or other device as described above.

The method is preferably practiced without a median sternotomy or other form of gross thoracotomy, i.e., with the patient's sternum and ribs substantially intact. In some cases, it may be desirable to form a small incision between the ribs, known as a mediastinotomy or mini-thoracotomy, which in some circumstances may involve the cutting or removal of one or more of the costal cartilages which connect the ribs to the sternum. In any event, the incision or opening formed in the patient's chest may be as small as practicable under the circumstances of the case, generally being smaller than the hands of the surgeon, usually having a length of less than about 8 cm, and preferably having a length of less than about 6 cm, with a width not much wider than the distance between the ribs, e.g., about 20–30 mm. In a particularly preferred embodiment, the cardioplegia catheter will be placed through a cannula, trocar or other retractor placed within an intercostal space between the ribs, and guided into the heart using long-handled thoracoscopic instruments positioned in the chest via intercostal access ports. The surgeon may visualize the interior of the chest either directly through such access ports, or using a thoracoscope and video camera. Placement of the occlusion balloon in the ascending aorta may be visualized using transesophageal echocardiography or fluoroscopy.

A further understanding of the nature and advantages of the invention will become apparent from the following detailed description taken in conjunction with the drawings.

BRIEF DESCRIPTION OF THE DRAWINGS

FIG. 1 is a side cross-sectional view of a cardioplegia catheter according to the invention.

FIG. 2 is a transverse cross-section of the cardioplegia catheter of FIG. 1 taken along line 2—2.

FIG. 8 is a side view of a cardioplegia catheter according to the invention in a second embodiment thereof.

FIG. 9 is a transverse cross-section of the cardioplegia catheter of FIG. 8 taken along the lines 9—9.

FIG. 15 is a side partial cross-section of a further embodiment of a cardioplegia catheter system according to the invention.

FIG. 16 is a transverse cross-section of the cardioplegia catheter system of FIG. 15 taken along line 16—16.

FIG. 18 is a partial cross-section of a patient's heart illustrating a further embodiment of a cardioplegia catheter system according to the invention.

DETAILED DESCRIPTION OF SPECIFIC EMBODIMENTS

Figure 10:
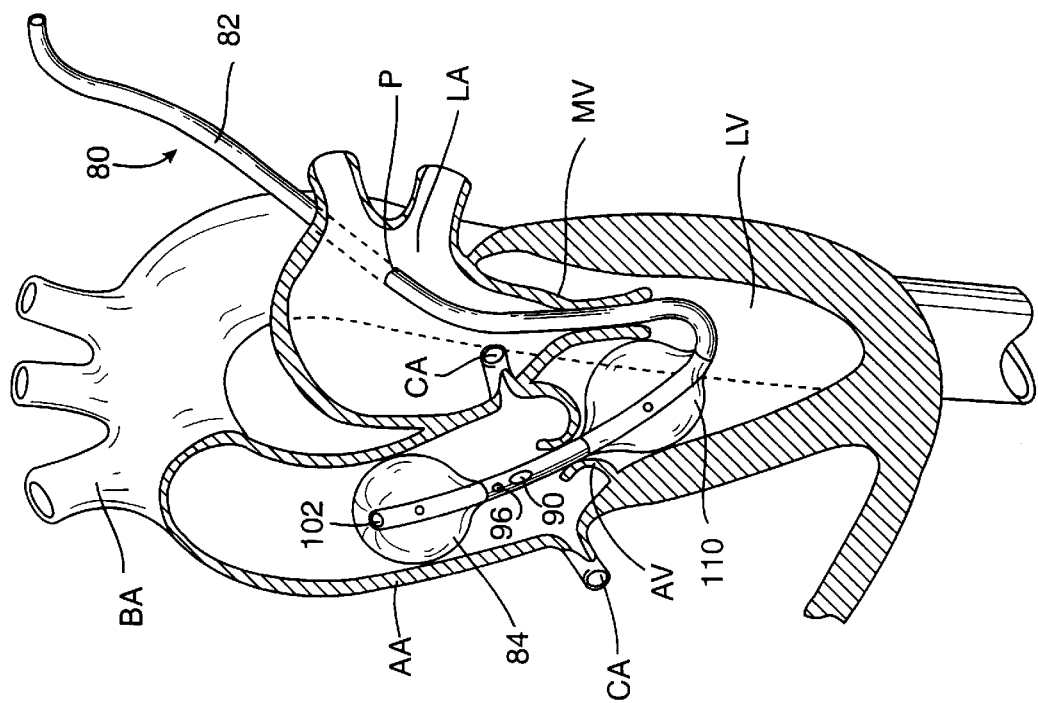
FIG. 10 is a partial cross-section of a patient's heart illustrating the positioning of the cardioplegia catheter of FIG. 8.

Referring to FIG. 1, a first embodiment of a cardioplegia catheter according to the invention will be described. Cardioplegia catheter 20 has a shaft 22 having a distal end 24 and a proximal end 26. An occlusion balloon 28 is attached to shaft 22 near distal end 24 by adhesive bonding or other known technique. One or more radiopaque bands or markers 29 are provided on shaft 22 adjacent occlusion balloon 28 to permit fluoroscopic imaging of the catheter within the aorta.

Shaft 22 has a plurality of lumens, as shown in FIG. 2. A first lumen 30 extends from a first port 32 at proximal end 26 to a first opening 34 proximal to occlusion balloon 28. A second lumen 38 extends from a second port 40 at proximal end 26 to a second opening 42 proximal to occlusion balloon 28. The positions of first and second openings 34, 42 are selected such that the openings will be disposed within the ascending aorta downstream of the aortic valve when occlusion balloon 28 is disposed between the brachiocephalic artery and the coronary arteries, as described more fully below. First and second openings 34,42 are preferably positioned within about 1 cm from the proximal end of occlusion balloon 28. A pressure monitoring device may be connected to second port 40 for monitoring pressure in the aortic root through second lumen 38.

First lumen 30 and first opening 34 are dimensioned to allow cardioplegic fluid to be delivered at sufficient rates to induce cardioplegic arrest effectively and rapidly. Usually, first lumen 30 will be configured for delivery of a cardioplegic fluid containing blood, which has been shown to more effectively protect the myocardium while the heart is arrested. In such cases, it is important that first lumen 30 allow the cardioplegic fluid to be delivered at sufficient rates to rapidly flow from the aortic root into the coronaries, perfuse the myocardium, and arrest the heart, without requiring the fluid to be delivered at excessive pressures which could damage the blood cells contained in the fluid. Preferably, first lumen 30 will permit delivery of cardioplegic fluid at rates of at least about 150 ml/min and at pressures no more than about 350 mmHg. Thus, first lumen 30 usually has a transverse cross-sectional area of about 2.0–3.0 mm$^2$, and preferably about 2.4–2.8 mm$^2$, between first port 32 and first opening 34.

A third lumen 44 extends from a third port 46 to a third opening 48 distal to occlusion balloon 28, usually being at distal end 24 of shaft 22. As shown in FIG. 1, occlusion balloon 28 may be configured to extend beyond the distal end of shaft 22 in an inflated configuration, but includes a central passage 49 communicating with third opening 48 such that third opening 48 communicates with the aortic lumen distally of the occlusion balloon. Third lumen 44 is usually configured to deliver oxygenated blood into the aorta at rates sufficient to sustain the patient on full cardiopulmonary bypass with the heart stopped, without reaching such high pressures as to cause excessive hemolysis, preferably allowing blood flow rates of at least about 4 liters/min at pressures no higher than about 350 mmHg. Third lumen 44 therefore has a cross-sectional area of at least about 20 mm$^2$, and preferably about 30–60 mm$^2$, between third port 46 and third opening 48, although the necessary cross-sectional area will vary depending upon the length of the catheter. Alternatively, as described more fully below, a separate arterial return cannula may be placed in an artery downstream of occlusion balloon 28 to return oxygenated blood to the patient instead of or as a supplement to arterial return through third lumen 44, in which case third lumen 44 may have a cross-sectional area that is significantly smaller.

An inflation lumen 50 extends from an inflation port 52 to an inflation opening 54 disposed within the interior of occlusion balloon 28. A source of inflation fluid, such as saline (preferably mixed with a radiopaque contrast agent) may be delivered through inflation lumen 50 into the interior of occlusion balloon 28 to inflate the balloon.

Preferably, occlusion balloon 28 is a compliant, elastic material such as silicone, urethane, or latex and is bonded to shaft 22 by adhesive, thermal, or solvent bonding. Occlusion balloon 28 is configured to expand to a size sufficient to engage the inner wall of the aorta and fully occlude the aortic lumen to block blood flow through it. The compliance of the balloon allows it to be expanded to a range of diameters so as to occlude aortas of various size, usually being inflatable to an outer diameter of at least about 20 mm and preferably about 20–40 mm for adult patients. Occlusion balloon 28 has an axial length (parallel to the longitudinal axis of shaft 22) short enough to allow it to occlude the ascending aorta without blocking either the brachiocephalic artery or the coronary arteries, preferably having a length in a range of about 20–50 mm for adult patients.

Figure 3A:
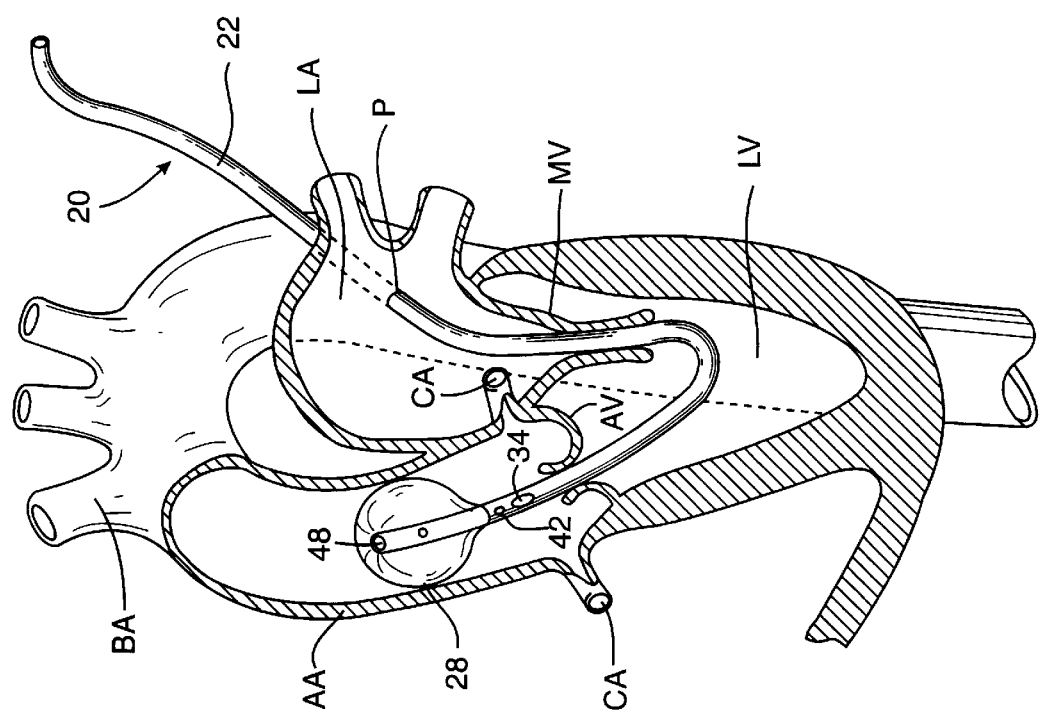
FIG. 3A is a partial cross-section of a patient's heart illustrating the positioning of the cardioplegia catheter of FIG. 1.
Figure 3B:
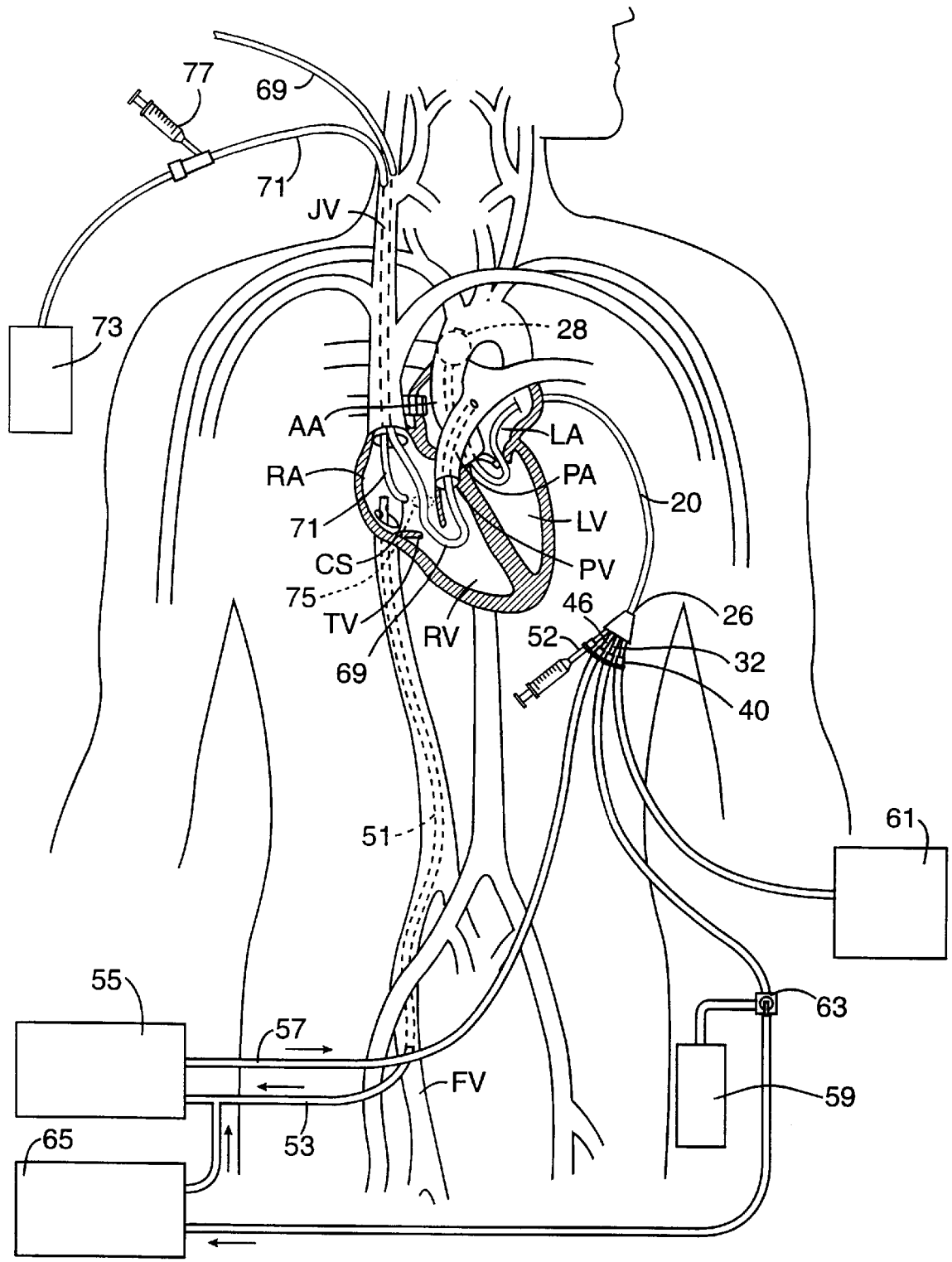
FIG. 3B is a schematic view of a cardiopulmonary bypass system and associated catheters used in a patient's body in conjunction with the cardioplegia catheter of FIG. 1.

FIGS. 3A–3B illustrate the cardioplegia catheter of FIGS. 1–2 in use in a patient's heart. With occlusion balloon 28 positioned in the ascending aorta AA between brachiocephalic artery BA and coronary arteries CA, shaft 22 extends through aortic valve AV, left ventricle LV, mitral valve MV and a puncture P in the wall of left atrium LA. Preferably, shaft 22 extends out of the patient's chest through a percutaneous incision, trocar sleeve or other small access port (not shown) placed in an intercostal space between the ribs, without creating a median sternotomy or other type of gross thoracotomy.

Once the cardioplegia catheter is positioned as shown, the patient may be placed on cardiopulmonary bypass, whereby blood is withdrawn from a vein through venous cannula 51, directed via venous line 53 to an extracorporeal cardiopulmonary bypass system 55 for oxygenation, and pumped via arterial return line 57 back into the aorta through third port 46, third lumen 44 and third opening 48. Preferably, venous cannula 51 extends transluminally from a femoral vein FV through the inferior vena cava and into the right atrium to remove blood from the heart. Cardiopulmonary bypass system 55 may be of known construction, including a pump for applying negative pressure to venous cannula 51, an oxygenator for oxygenating the withdrawn blood, a bubble trap for removing air bubbles from the blood, and an additional pump for returning the blood to the arterial system. Other components and features of cardiopulmonary bypass systems that may be employed in the system of the present invention will be apparent to those of skill in the art.

Occlusion balloon 28 may then be inflated to occlude ascending aorta AA, and cardioplegic fluid may be delivered from a pressurized fluid source 59 through first port 32, first lumen 30 and first opening 34 to perfuse the myocardium via coronary arteries CA, thereby arresting cardiac function. Preferably, cardioplegic fluid source 59 is configured to deliver a cardioplegic fluid comprising blood plus a cardioplegic agent such as potassium chloride, which has been found to optimally protect and preserve the myocardium during the procedure. Pressure in the aortic root may be monitored through second lumen 38 and second opening 42, which are connected to a pressure monitoring system 61 outside the patient's body. Venting of the aortic root proximally of balloon 28 may be accomplished by turning a valve 63 so that first lumen 30 is in communication with blood filtering and recovery module 65 instead of cardioplegic fluid source 59. Blood, fluids and any embolized materials removed from the aorta are filtered by module 65 and the filtered blood is returned to the body via cardiopulmonary bypass system 55.

In an additional aspect of the invention, illustrated in FIG. 3B, a pulmonary artery catheter 69 and coronary sinus catheter 71 are utilized in conjunction with cardioplegia catheter 20. These catheters may be introduced transluminally into the heart from a peripheral vein such as internal jugular vein JV. Pulmonary artery catheter 69 is advanced from right atrium RA through the tricuspid valve TV, right ventricle RV and pulmonary valve PV into the pulmonary artery PA. The catheter is connected at its proximal end to a pump or other fluid aspiration device. Any blood or fluids not removed by venous cannula 51 that reach the pulmonary artery may be removed through pulmonary artery catheter PV, thereby keeping the heart adequately vented. Blood removed through pulmonary artery catheter 69 may be returned to blood filter/recovery module 65 for treatment and return to the body via cardiopulmonary bypass system 55. Other aspects of pulmonary artery catheters suitable for use in conjunction with the present invention are described in copending application Ser. No. 08/415,238, filed Mar. 30, 1995, which is incorporated herein by reference.

Coronary sinus catheter 71 is advanced from jugular vein JV and right atrium RA into the coronary sinus CS, through which blood ordinarily drains from the coronary arteries and veins into the right side of the heart. Coronary sinus catheter 71 preferably includes a main lumen extending through its length to an opening at its distal end, allowing cardioplegic fluids to be delivered from a pressurized fluid source 73 to the myocardium in a retrograde manner via the coronary veins. To facilitate this process, coronary sinus catheter 71 preferably includes a balloon 75 at its distal tip configured to occlude the coronary sinus during delivery of cardioplegic fluids. Balloon 75 is inflated by delivery of a fluid such a saline from a syringe 77 or other suitable inflation device via an inflation lumen in communication with balloon 75. In this way, cardioplegic fluid may delivered through the coronary sinus catheter 71 either in conjunction with cardioplegic fluid delivery through cardioplegia catheter 20, or as a substitute for delivery through cardioplegia catheter 20. Other aspects of coronary sinus catheters suitable for use in conjunction with the present invention are described in U.S. Pat. No. 5,558,644, which is incorporated herein by reference.

Figure 4:
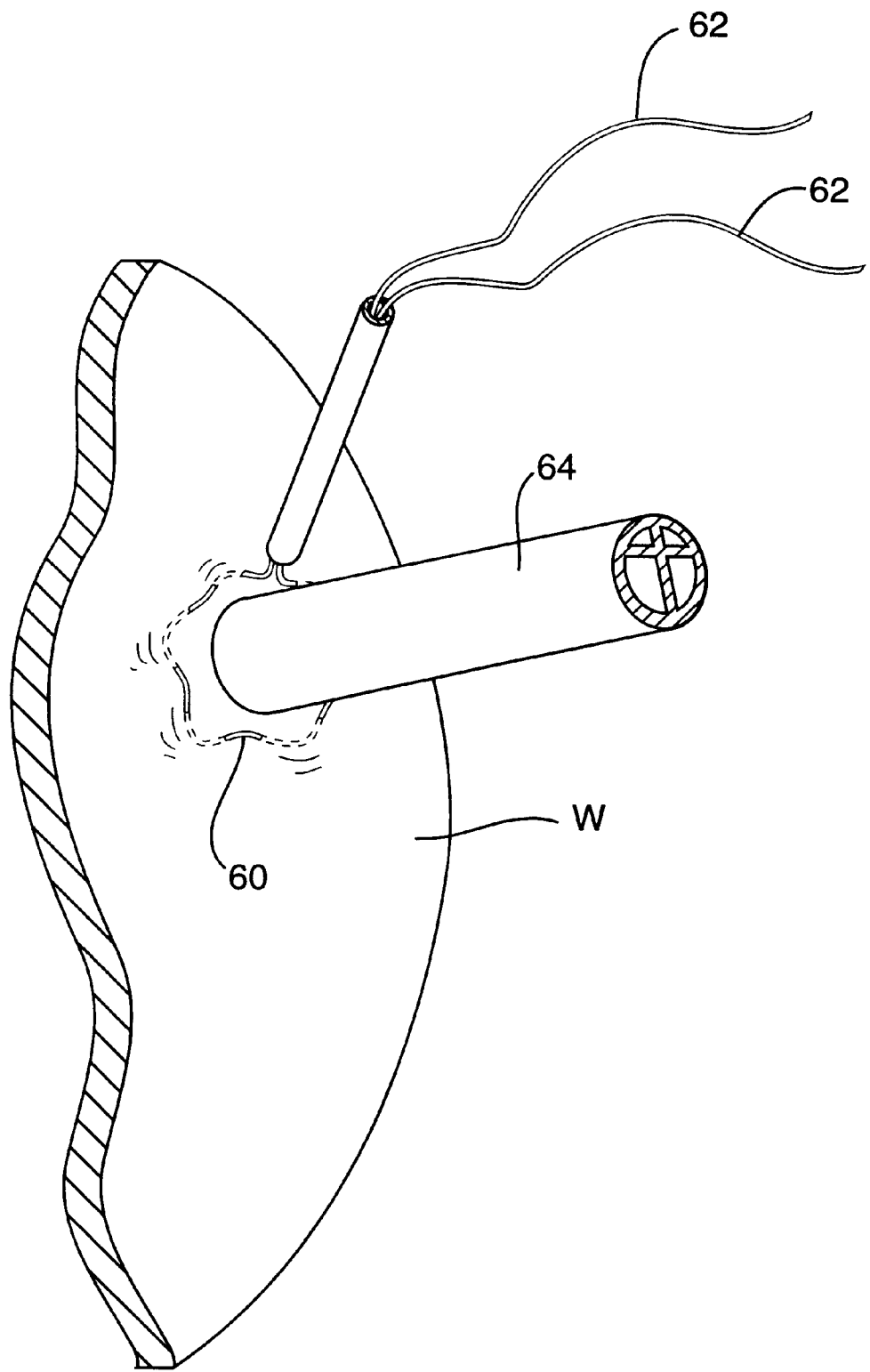
FIG. 4 is an elevational view of an outer wall of a patient's heart illustrating the placement of a purse-string suture around a penetration therein.
Figure 6:
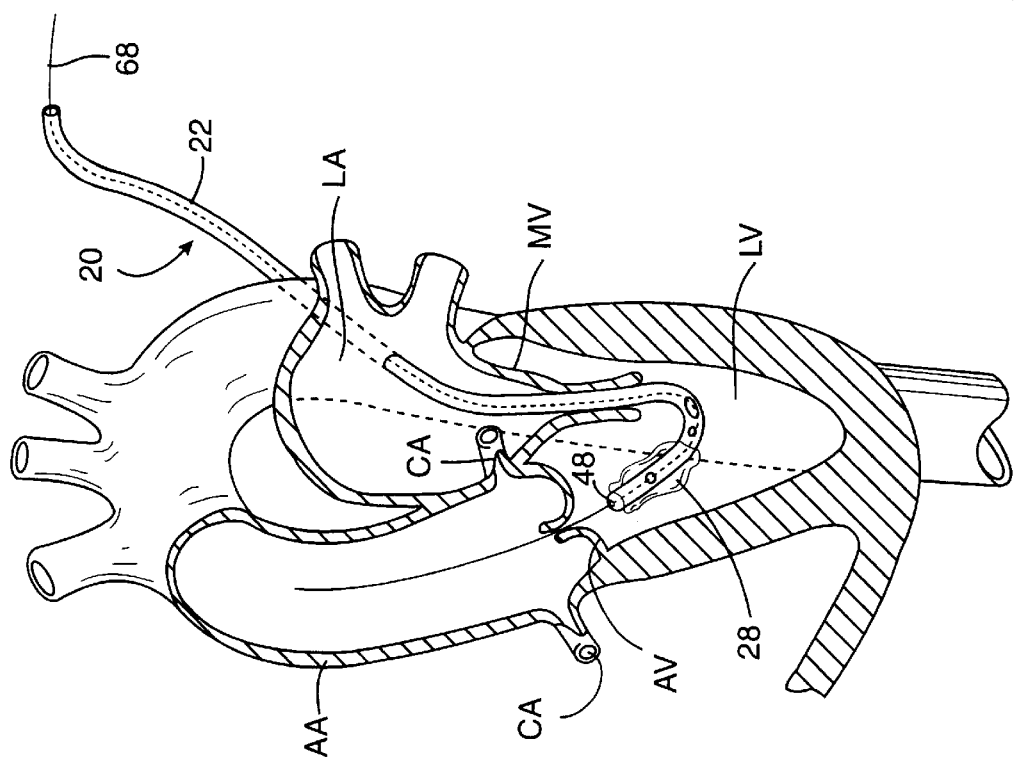
FIGS. 5–7 are partial cross-sections of a patient's heart illustrating the introduction of the cardioplegia catheter of FIG. 1 into the ascending aorta.
Figure 5:
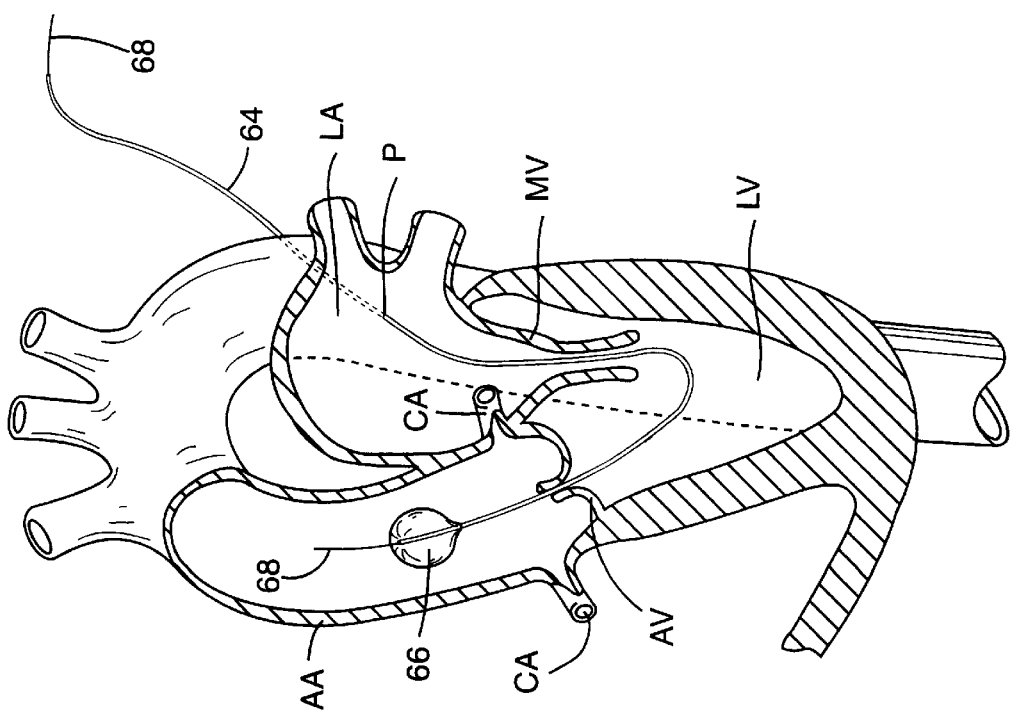

A preferred technique of positioning cardioplegia catheter 20 in the ascending aorta is shown in FIGS. 4–6. In this technique, a purse-string suture 60 is placed in the left atrial wall W around the intended site of catheter introduction, as shown in FIG. 4. Suture 60 may be placed using well-known techniques, and is preferably placed using thoracoscopic instruments introduced through small incisions, trocar sleeves or other intercostal access ports not requiring a gross thoracotomy. The left atrium may be accessed via access ports in the 3$^{rd}$, 4$^{th}$ or 5$^{th}$ intercostal spaces on the right lateral or right anterior side of the chest. If desired, the heart may be repositioned within the chest to improve access using thoracoscopic retraction instruments introduced through access ports between the ribs. Once purse-string suture 60 has been placed in wall W, a small incision or puncture P is formed in wall W so as to be encircled by suture 60, and a flow-directed catheter 64, shown in FIG. 5, is inserted through puncture P. The free ends 62 of suture 60 may then be tensioned so as to form a seal between wall W and the outer wall of flow-directed catheter 64. Preferably, a suture tensioner 66 is used to maintain tension on suture ends 62, which may consist of a tube 68 having an inner lumen 70 through which ends 62 may be passed. Lumen 70 is dimensioned to frictionally engage suture ends 62 so as to maintain adequate tension on suture S to create a hemostatic seal around catheter 64.

Once positioned in the left atrium LA, as shown in FIG. 5, flow-directed catheter 64 is advanced through the mitral valve MV into left ventricle LV, and through aortic valve AV into the ascending aorta AA. To assist such positioning, flow-directed catheter 64 has an expandable member 66 at its distal end which, when expanded, is carried by the flow of blood through the heart into the ascending aorta. Expandable member 66 is usually a balloon that is inflated with fluid introduced through an inflation lumen (not shown in FIG. 5) extending through the flow-directed catheter into the interior of the balloon. Expandable member 66 may be inflated in the left atrium LA, from which blood will carry it through the mitral and aortic valves into the aorta. Flow-directed catheter also includes a guidewire lumen (not shown in FIG. 5) through which a guidewire 68 may be positioned either during or after flow-directed catheter is positioned in ascending aorta AA. Guide wire 68 is advanced through flow-directed catheter 64 until its tip is in ascending aorta AA, and flow-directed catheter is then removed from the patient, leaving guidewire 68 in position in the heart. As the flow-directed cathteter is removed from left atrial wall W, purse-string suture S is tensioned to maintain a hemostatic seal around guidewire 68.

As shown in FIG. 6, the proximal end of guidewire 68 is then placed in third lumen 44 in cardioplegia catheter 22 outside the heart, and cardioplegia catheter 22 is slidably advanced over guidewire 68 through puncture P, mitral valve MV, and aortic valve AV into ascending aorta AA. Guidewire 68 is then removed from third lumen 44, leaving cardioplegia catheter 20 in the position of FIG. 3.

Figure 7:
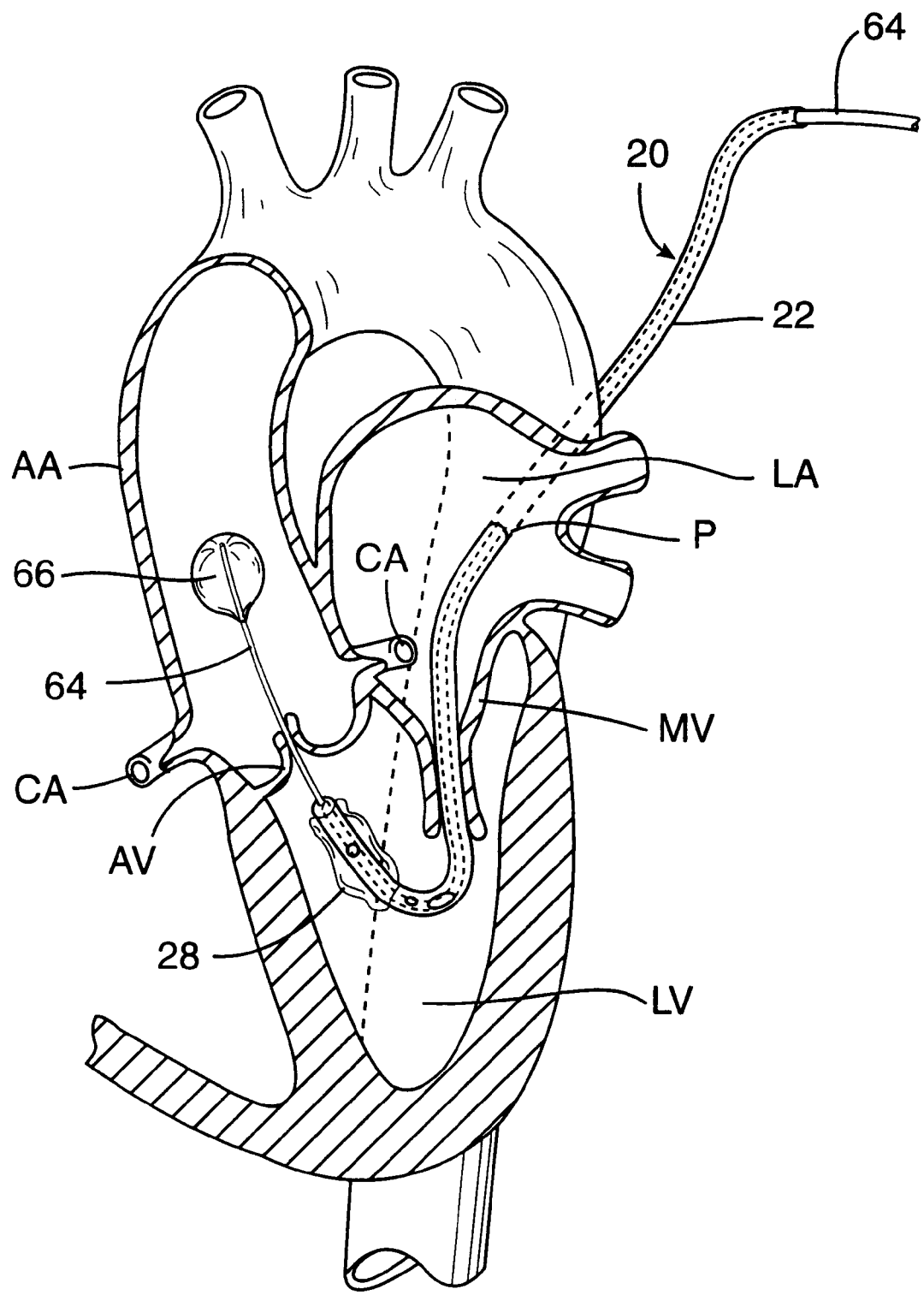

As an alternative to the use of a guidewire, cardioplegia catheter 20 may be configured to be advanced into the ascending aorta AA directly over flow-directed catheter 64, as shown in FIG. 7. In this embodiment, flow-directed catheter 64 need not have a guidewire lumen, allowing it to be smaller and more flexible. Once cardioplegia catheter 20 has been slidably advanced over flow-directed catheter 64 into ascending aorta AA, expandable member 66 is deflated and the flow-directed catheter is withdrawn from third lumen 44.

As may be seen in FIG. 3, shaft 22 of cardioplegia catheter 20 must be shapable into a curve of very small radius in order to extend through both the aortic valve AV and mitral valve MV, a distal portion of the shaft which extends through the aortic valve being at an angle of around 100–170 degrees, preferably about 110 to 150 degrees, relative to the proximal portion of the shaft which extends through the mitral valve. Preferably, shaft 22 will be reinforced in at least the region of this curve with a wire winding (not shown) embedded in its outer wall to prevent the shaft from kinking. Suitable wire-wound shafts and methods of manufacturing such shafts are described in copending application Ser. No. 08/664,716, filed Jun. 17, 1996, which is incoroporated herein by reference.

In addition to wire winding or other form of reinforcement, shaft 22 may be preshaped in a curve to facilitate positioning the catheter through the mitral and aortic valves. The preshaped portion of the shaft will preferably be shaped such that a distal portion of the shaft is disposed at an angle of about 90–150 degrees relative to the proximal portion of the shaft. The curve will usually be disposed about 4–8 cm from the distal end of shaft 22 for use in adult patients. When introducing cardioplegia catheter 20 through puncture P, a stylet (not shown) may by positioned in third lumen 44 to straighten the preshaped portion. The stylet is gradually withdrawn from the catheter as it is advanced through the mitral valve into the left ventricle.

As another alternative, cardioplegia catheter 20 may have a generally straight shaft 22, but a steerable or shapable stylet may be provided which is removably positionable in first lumen 30 or third lumen 44. In a shapable embodiment, the stylet is a malleable material which permits it to be in elastically shaped into the desired configuration, then placed into a lumen in shaft 22 to impart such shape to the shaft. Once distal end 24 of cardioplegia catheter 20 has been placed through the mitral valve, the shaped stylet may be placed in either of lumens 30 or 44 to orient distal end 24 in a suitable position for advancement through the aortic valve. In a steerable embodiment, the stylet includes a steering mechanism such as one or more pull wires extending through a lumen in the stylet and fastened to its distal end, offset from the radial center of the stylet. By exerting tension on the pull wires, the distal end of the stylet may be deflected into a curved or bent shape. In this way, once cardioplegia catheter 20 has been advanced through the mitral valve, the stylet may be inserted in lumen 44 and deflected so as to re-orient distal end 24 of shaft 22 in a suitable orientation for advancement through the aortic valve.

As a further alternative, cardioplegia catheter 20 itself may include a steering mechanism for steering the distal end of shaft 22 through the mitral and aortic valves. For example, one or more pull wires may extend through a lumen in shaft 22 and be fastened near distal end 24, offset from the radial center of the shaft. By tensioning the pull wires, the distal portion of the shaft can be deflected into a curved or bent shape suitable for placement from the mitral valve through the aortic valve.

A second embodiment of a cardioplegia catheter 80 according to the invention is illustrated in FIGS. 8–10. Cardioplegia catheter 80 is in many respects similar to cardioplegia catheter 20 of FIGS. 1–7, having a flexible shaft 82, an occlusion member 84 at the distal end of shaft 82, a first lumen 86 extending from a first port 88 to a first opening 90 proximal to occlusion member 84, a second lumen 92 extending from a second port 94 to second opening 96 proximal to occlusion member 84, and a third lumen 98 extending from a third port 100 to a third opening 102 distal to occlusion member 84. Occlusion member 84 is preferably an occlusion balloon, inflated by means of inflation fluid delivered through an inflation lumen 104 extending from an inflation port 106 to an inflation opening 108 within the occlusion balloon.

Unlike the previous embodiment, cardioplegia catheter 80 further includes a ventricular balloon 110 spaced proximally from occlusion member 84 and first and second openings 90, 94. The position of ventricular balloon 110 on shaft 82 is selected such that it will be disposed in the left ventricle adjacent the aortic valve when occlusion balloon 84 is in the ascending aorta between the brachiocephalic artery and the coronary arteries, usually being positioned about 4–8 cm proximally of occlusion balloon 84 for use in adult patients. Ventricular balloon 110 is inflated via a second inflation lumen 112 extending from a second inflation port 114 at the proximal end of the shaft to a second inflation opening in shaft 82 within the ventricular balloon. The balloon will preferably be inflatable to a diameter of about 2–4 cm to facilitate occlusion of the ventricular outflow tract at the around the annulus of the aortic valve.

Cardioplegia catheter 80 of FIGS. 8–9 is shown in position in a patient's heart in FIG. 10. The catheter may be introduced from a puncture P in the left atrium LA, through the mitral valve MV, left ventricle LV, and aortic valve AV in the manner described above in connection with FIGS. 4–7. When ventricular balloon 110 is positioned in the left ventricle LV, it may be inflated so as to prevent further advancement of cardioplegia catheter 80 into the aorta. Ventricular balloon 110 is seated within the left ventricular outflow tract in engagement with the ventricular wall around the annulus of the aortic valve. With cardiopulmonary bypass established and oxygenated blood being returned to the arterial system via third lumen 98 or through a separate arterial cannula, occlusion balloon 84 is expaned to occlude the ascending aorta AA, preventing arterial blood from reaching the coronary arteries CA. Cardioplegic fluid is then delivered through first lumen 86 into the aorta proximal to occlusion balloon 84, from which the fluid may flow into the coronary arteries to perfuse the myocardium and arrest the heart. It may be seen that, with shaft 82 extending through aortic valve AV, some cardioplegic fluid could flow around shaft 82 through the aortic valve leaflets into the left ventricle LV. Advantageously, ventricular balloon 110 occludes the left ventricular outflow tract around the aortic valve annulus, preventing flow of fluid into the left ventricle.

The invention provides a number of different alternatives for returning oxygenated blood to the patient's arterial system downstream from the occlusion member of the cardioplegia catheter. In one embodiment, described above, oxygenated blood is returned to the aorta through third lumen 44 in cardioplegia catheter 20 or third lumen 98 in cardioplegia catheter 80. This has the advantage of eliminating the need for a separate arterial cannula and the associated arterial incision through which the cannula would be placed. However, in some cases, it may be desirable to decouple the arterial return device from the cardioplegia catheter so that if the need arises to remove the occlusion member from the ascending aorta, it can be rapidly removed without removing the arterial cannula, which would require the patient to be weaned from cardiopulmonary bypass. To provide this advantage, a separate arterial cannula may be used in addition to or instead of the third lumen in the cardioplegia catheter.

Figure 11:
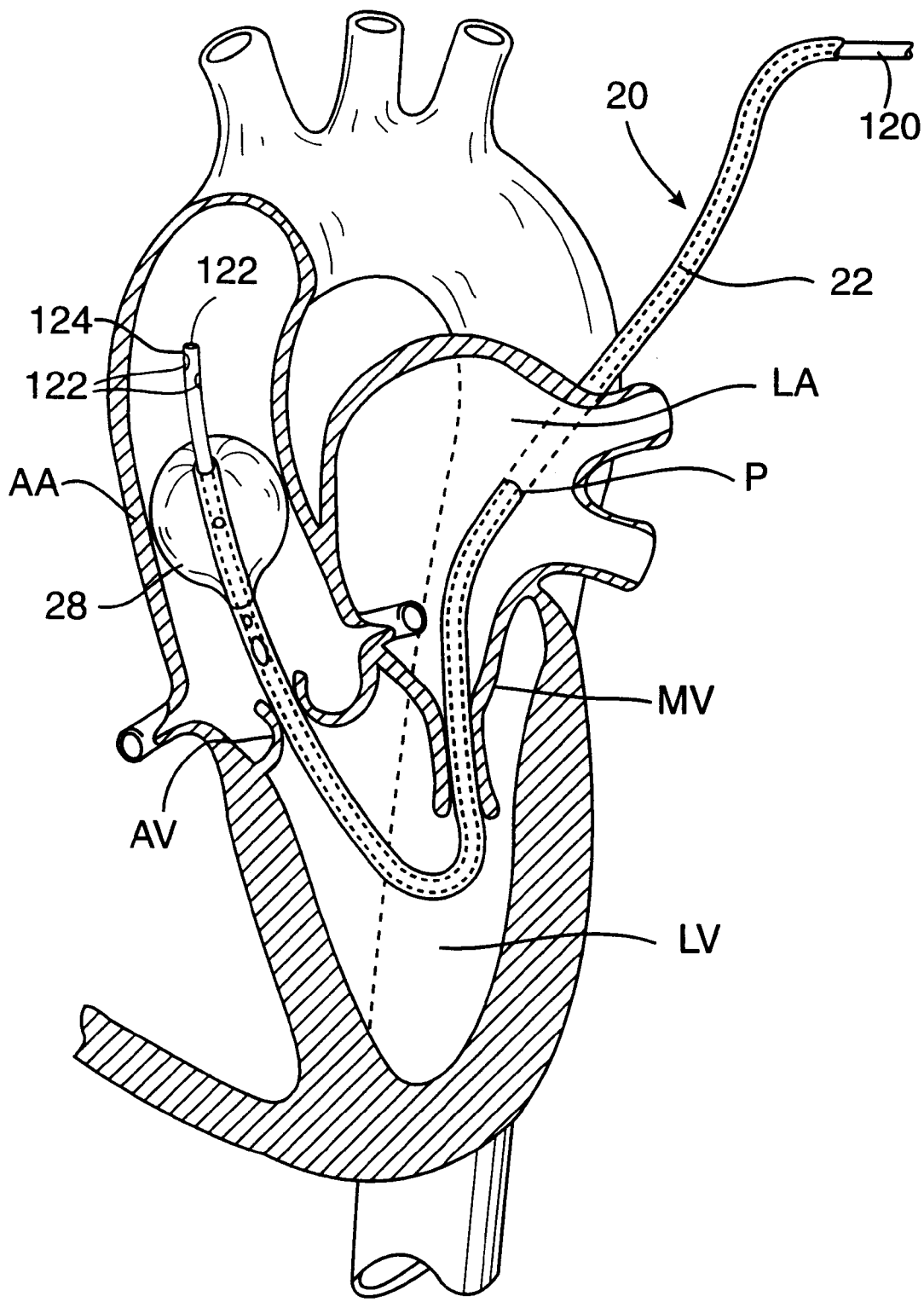
FIGS. 11–14 are partial cross-sections of a patient's heart illustrating various embodiments of arterial return cannulas according to the invention.

In one embodiment, shown in FIG. 11, an arterial return cannula 120 is slidably positioned through third lumen 44 in cardioplegia catheter 20. Arterial return cannula 120 is configured to deliver oxygenated blood into the aorta at rates sufficient to sustain the patient on full cardiopulmonary bypass with cardioplegic arrest, having a blood flow lumen and one or more outlets 122 at its distal end 124 with dimensions similar to those described above in connection with third lumen 44 of the cardioplegia catheter. In use, cardioplegia catheter 20 is first positioned in the ascending aorta in the manner described above. Arterial return cannula 120 is then slidably advanced through third lumen 44 until distal end 122 is positioned in ascending aorta AA. Arterial return cannula 120 is connected at its proximal end to the extracorporeal cardiopulmonary bypass circuit so as to receive oxygenated blood and deliver it into the aorta. Occlusion balloon 28 may then be inflated to occlude the ascending aorta, and cardioplegic fluid delivered through first lumen 30 to arrest the heart. Should the need arise to remove occlusion balloon 28 from the aorta during the procedure, occlusion balloon 28 is deflated, and cardioplegia catheter 20 slidably retracted over arterial cannula 120, which may continue to deliver blood into the arterial system.

Figure 12:
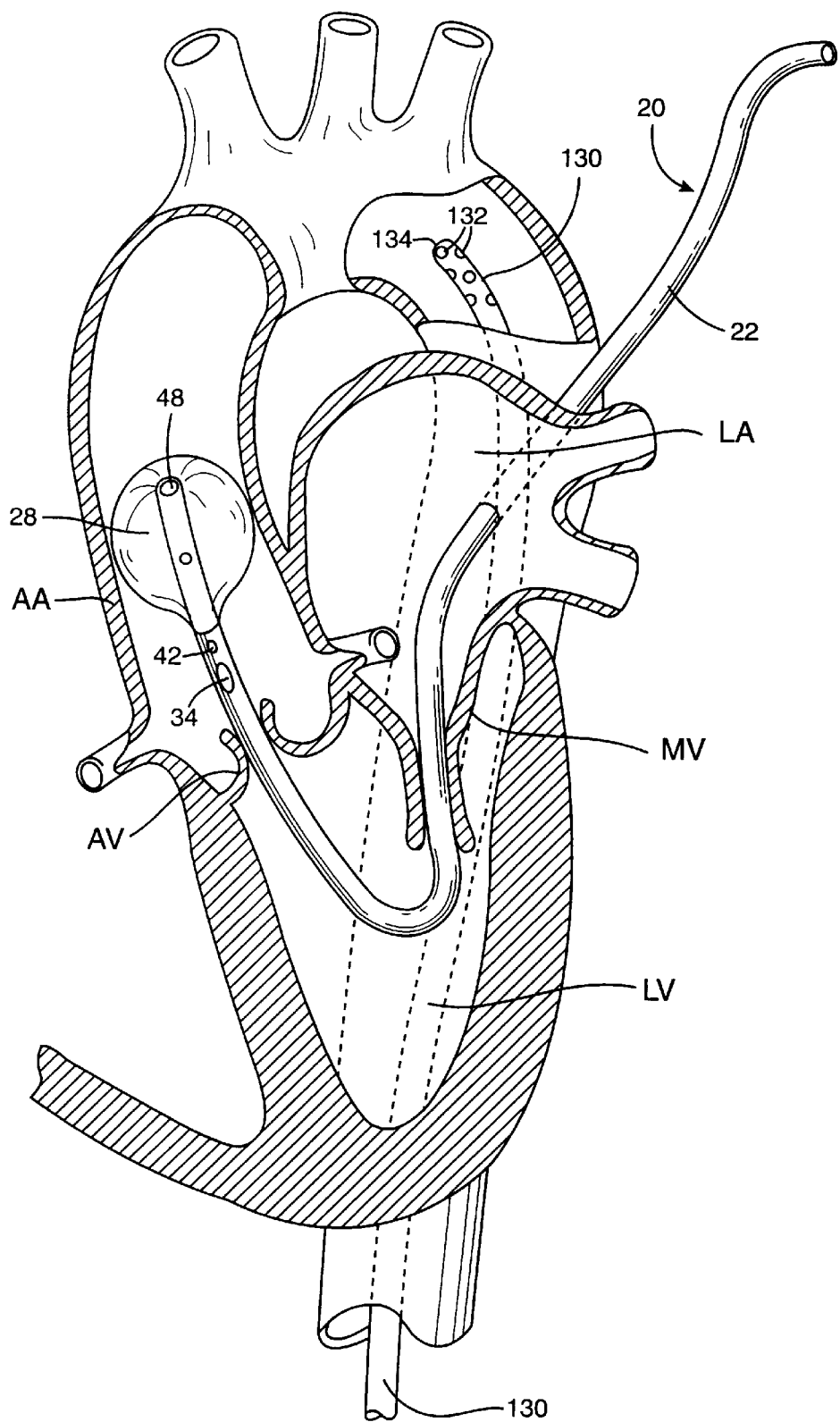

In an alternative embodiment, shown in FIG. 12, an arterial return cannula 130 is configured for introduction in a femoral or iliac artery. Arterial return cannula 130 may be short, e.g. 4–10 cm, so as to extend only into the iliac or abdominal aorta, but is preferably at least about 80 cm long so as to extend into the thoracic aorta or aortic arch as shown. In this way, blood may be returned to the aorta near the vessels at the top of the arch that deliver blood to the head and neck, and allowing blood to flow in the natural, antegrade direction through the aorta, iliac and femoral arteries. Arterial return cannula 130 is again configured to deliver blood at sufficient rates to support the patient on full cardiopulmonary bypass with the heart arrested, delivering flows of at least about 4 liters/min at pressures no higher than 350 mmHg. Arterial return cannula 130 has an inner lumen and outlets 132 at its distal end 134 with dimensions sufficient to provide such flows. At the same time, arterial return cannula 130 has outer dimension small enough to be positionable in a femoral artery of limited diameter. Usually, arterial return cannula 130 has an inner lumen with cross-sectional area of at least about 30 mm$^2$, preferably about 40–70 mm$^2$, and an outer diameter of no more than about 8 mm, preferably about 6–7 mm, for use in adult patients. Of course, if oxygenated blood is also returned through third lumen 44 of cardioplegia catheter 20, arterial return cannula 130 may have a smaller lumen.

Figure 13:
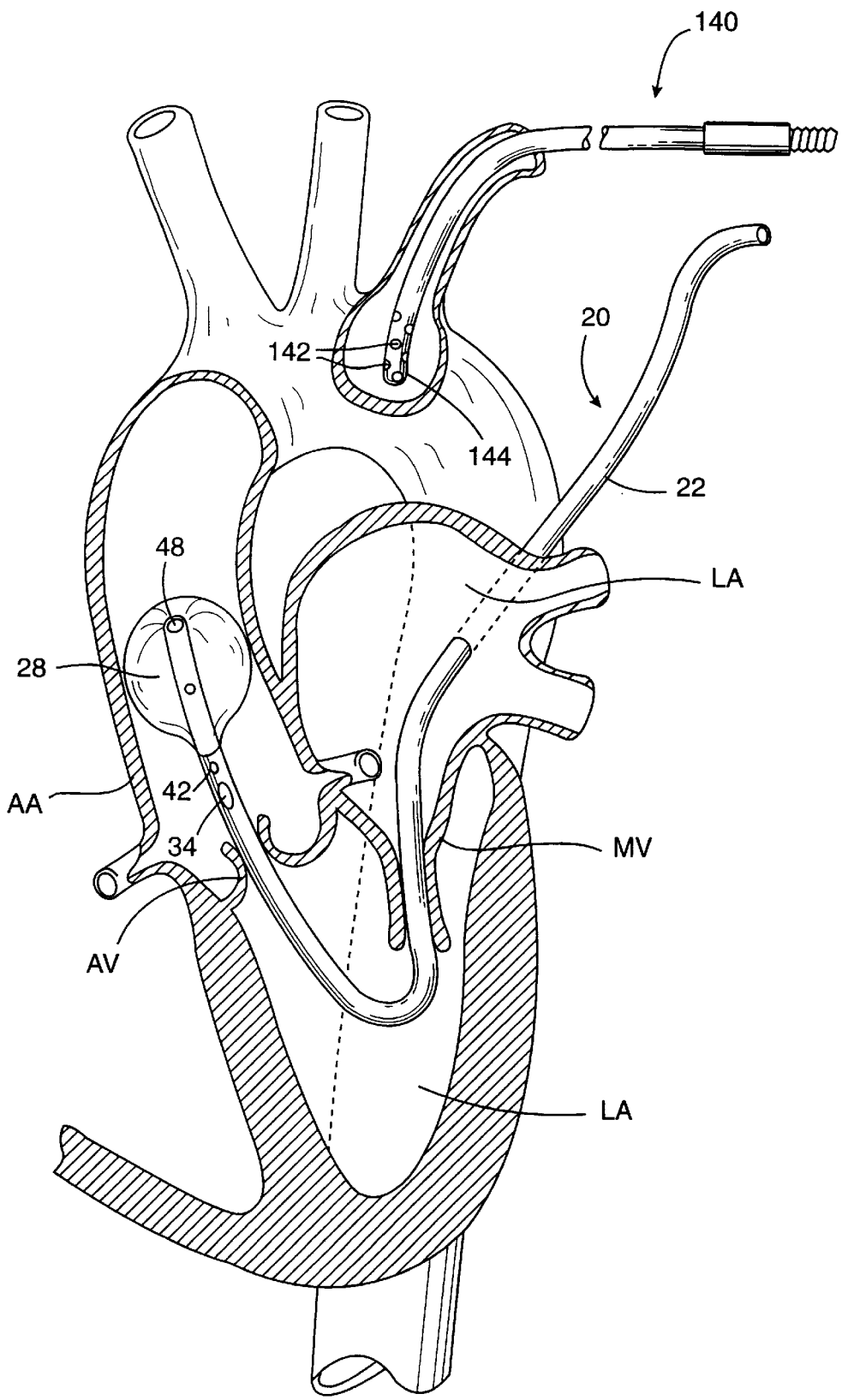

In a further embodiment, illustrated in FIG. 13, an arterial return cannula 140 is configured for placement in a subclavian or axillary artery and advanced into or near the aortic arch. In this way, arterial blood may be returned to the aorta near the top of the aortic arch so as to flow in an antegrade direction. Arterial return cannula has an inner lumen in communication with one or more openings 142 near its distal end 144, and preferably has a length of about 10–50 cm, an outer diameter of about 6–7 mm, and an inner lumen with cross-sectional area of about 30–50 mm² to deliver oxygenated blood at sufficient rates to sustain the patient on full cardiopulmonary bypass.

Figure 14:
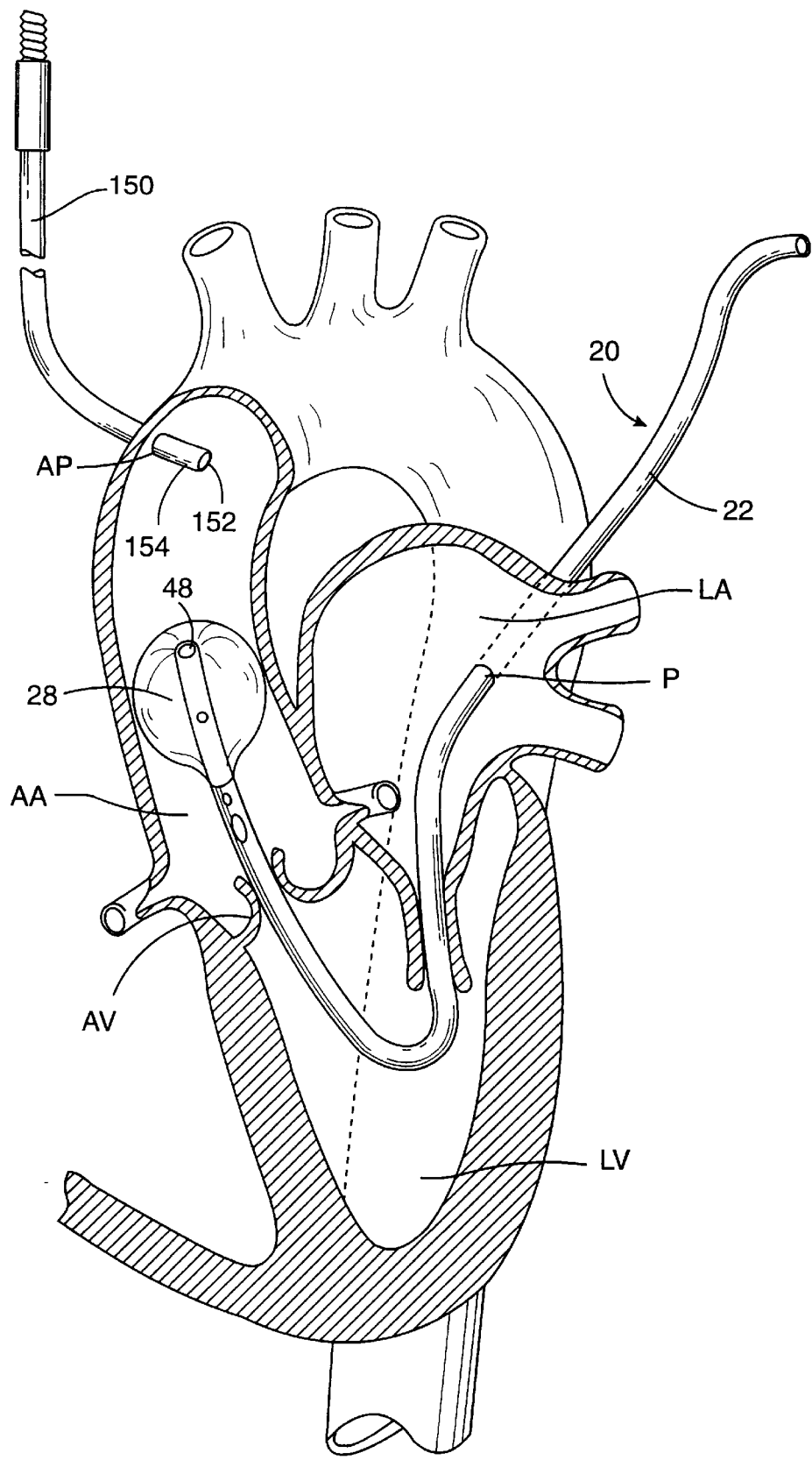

In another embodiment, shown in FIG. 14, an arterial return cannula 150 is configured to be placed thoracoscopically into the ascending aorta through an aortic puncture AP. Blood leakage through aortic puncture AP may be avoided by placing a purse-string suture (not shown) around the puncture similar to suture S placed in the left atrial wall, as described above in connection with FIG. 7. Arterial return cannula 150 is configured to direct oxygenated blood in a downstream direction in the aorta, having an inner lumen communicating with at least one outlet 152 at its distal end 154. The inner lumen of arterial return cannula 150 has a cross-sectional area of about 30–50 mm² so as to deliver blood at sufficient flows to maintain full cardiopulmonary bypass with the heart stopped. Arterial return cannula 150 further has a length of at least about 20 cm so as to extend out of the chest through a small incision, trocar sleeve, or access port in an intercostal space, without creating a gross thoracotomy.

Figure 17:
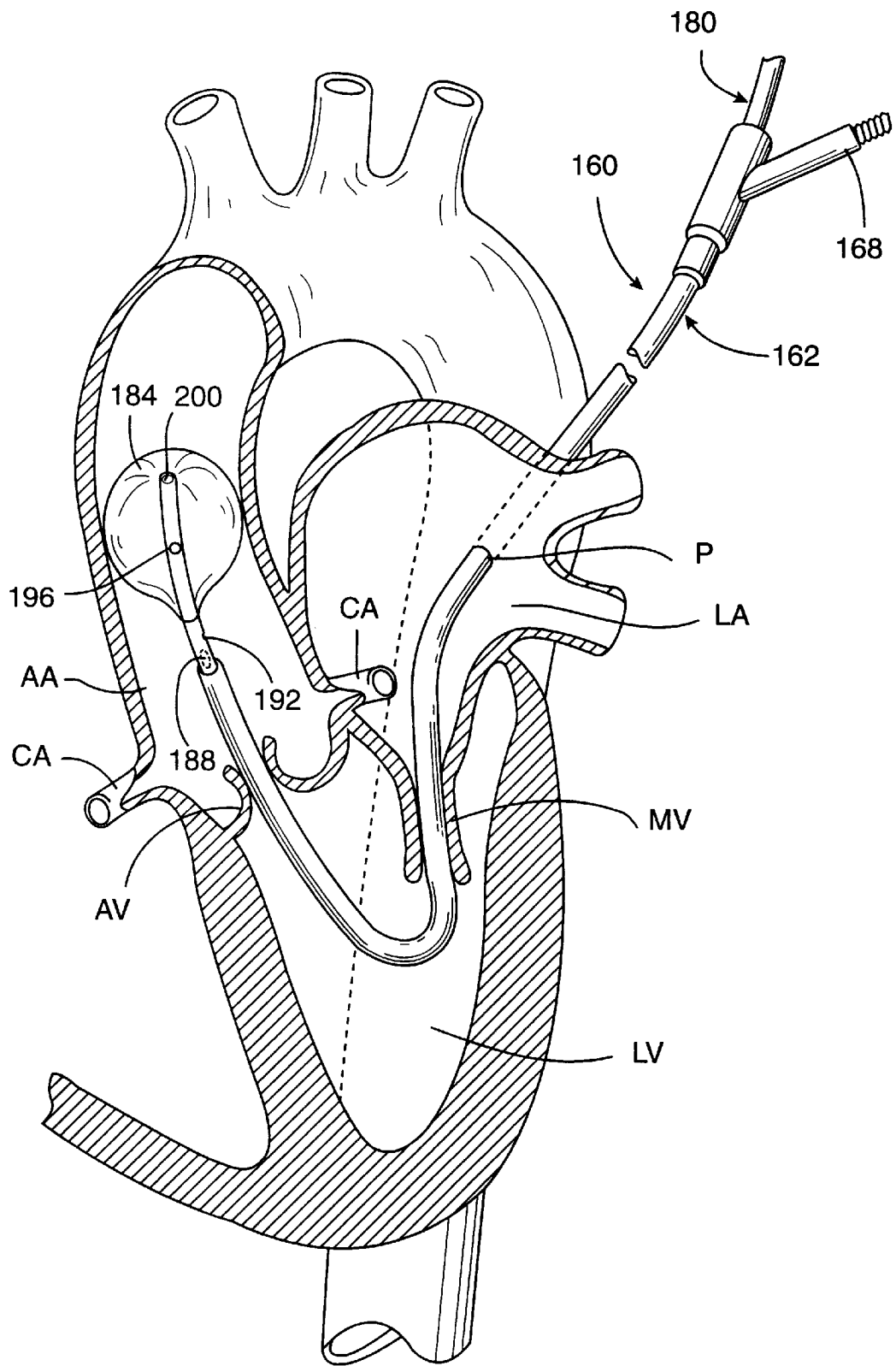
FIG. 17 is a partial cross-section of a patient's heart illustrating the use of the cardioplegia catheter system of FIG. 15.

An additional embodiment of a cardioplegia catheter system according to the invention is shown in FIGS. 15–17. In this embodiment, cardioplegia catheter system 160 includes an arterial return cannula 162 having a return lumen 164, a return opening 166 at its distal end and a return port 168 at its proximal end. A catheter port 170 is in communication with return lumen 164 at the proximal end of arterial cannula 162 and includes a hemostasis valve 172 for sealing around a catheter shaft positioned in the catheter port. Hemostasis valve 172 may be any of a variety of well known types, comprising, for example, a pair of parallel compliant elastomeric disks 174, 176, one having an axial slit (not shown) for sealing when the catheter shaft is absent, and one having a round axial hole (not shown) for sealing around the catheter shaft. Return port 168 includes a hose barb 178 for connection to standard tubing from an extracorporeal cardiopulmonary bypass circuit to receive oxygenated blood. A seal 179, which may be an elastomeric O-ring, is mounted near return opening 166 for sealing around a catheter shaft positioned therethrough.

A cardioplegia catheter 180 is slidably positionably positionable through catheter port 170, return lumen 164 and return opening 166. Cardioplegia catheter 180 has a multi-lumen shaft 182 and a balloon 184 mounted near its distal end configured to occlude the ascending aorta. Shaft 182 includes a first lumen 186 extending from a first opening 188 just proximal to balloon 184 to a first port (not shown) at the proximal end of the shaft. A pressure lumen 190 extends from a pressure opening 192 just proximal to balloon 184 to a pressure port (not shown) at the proximal end of the shaft. An inflation lumen 194 extends from an inflation opening 196 within balloon 184 to an inflation port (not shown) at the proximal end of the shaft.

A blood lumen 198 extends from a blood outlet 200 at the distal end of shaft 182 to a plurality of blood inlets 202 in the sidewall of shaft 182 in a proximal region thereof. Blood inlets 202 are positioned so as to be within return lumen 164 when balloon 184, first opening 188 and pressure opening 192 are disposed distally of the distal end of arterial return cannula 162. In this way, blood flowing through return lumen 164 flows into blood inlets 202 and through blood lumen 198 into the aorta distally of balloon 184. Blood lumen 198 is preferably configured to provide sufficient blood flow for full cardiopulmonary bypass with cardioplegic arrest, dimensioned to provide flows of at least 4 liters/min at pressures not exceeding 350 mmHg.

The positioning of cardioplegia catheter system 160 in the heart and ascending aorta is illustrated in FIG. 17. Usually, cardioplegia catheter 180 will first be positioned in arterial return cannula 162 and the two will placed through a penetration P in the left atrium LA (sealed by a purse-string suture), advanced through the mitral valve MV, through the aortic valve AV, and into the ascending aorta AA. A guide wire, stylet, or flow-directed catheter may be used to assist placement, as described above. Arterial blood flow is initiated through return port 168, from which the blood flows through blood lumen 198 and blood outlet 200 into the aorta. Balloon 184 is then inflated so as to occlude ascending aorta AA. A cardioplegic agent may then be delivered through first lumen 186 and first opening 188 so as to arrest the heart.

When it is desired to remove cardioplegia catheter 180 from the ascending aorta, it may be slidably withdrawn from return lumen 164 while arterial return cannula 162 remains in place, at which time blood flowing into return port 168 will flow directly through return lumen 164 into the aorta, thereby continuing to maintain circulation of oxygenated blood in the patient.

It should be understood that as an alternative to the embodiment illustrated, a single blood inlet port in communication with blood lumen 198 at the proximal end of cardioplegia catheter 180 may be provided in place of blood inlets 202. The oxygenated blood return line may be connected both to this blood inlet port and to return port 168 of the arterial cannula, preferably in series with a two-way valve to allow selective direction of blood flow between either port. In this way, when cardioplegia catheter 180 is positioned in return lumen 164, blood may be directed to the blood inlet port at its proximal end so as to flow into the aorta distally of balloon 184. When the cardioplegia catheter is removed, blood may be directed to flow through return port 168 to continue flow into the aorta through arterial return cannula 160.

FIG. 18 illustrates still another embodiment of a cardioplegia catheter system according to the invention. Cardioplegia catheter system 210 includes a tubular sheath 212 having distal end 214 configured for placement through a penetration P in the left atrium LA. Sheath 212 has an opening 216 at its distal end 214 and first and second ports 218, 220 at its proximal end, each of which preferably has a hemostasis valve (not shown) for sealing around a catheter shaft positioned therethrough. An arterial return cannula 222 is slidably positionable through first port 214 and sheath 212 and has a distal end 224 which may be advanced into the ascending aorta AA through mitral valve MV and aortic valve AV. Arterial return cannula 222 has a return opening 226 at its distal end, a return port 228 at its proximal end, and a return lumen (not shown) therebetween through which oxygenated blood may be delivered into the aorta.

Cardioplegia cannula 230 may be constructed similarly to cardioplegia cannula 20 described above in connection with FIGS. 1–3, having a balloon 232 for occluding the ascending aorta, a cardioplegia/venting opening 234 and pressure opening 236 proximal to balloon 232, and an inflation opening 238 within balloon 232, along with associated lumens and proximal ports 240, 242, 244 in communication with openings 234, 236, 238, respectively. A distal opening 246 and corresponding lumen are optionally provided to assist placement of the cardioplegia cannula over a guidewire or flow-directed catheter.

After arterial return cannula 222 has been positioned through sheath 212 and advanced into ascending aorta AA, cardioplegia catheter 230 is slidably introduced through second port 220 in sheath 212 and advanced through the heart into the ascending aorta AA. Balloon 232 is then inflated to occlude the ascending aorta AA between the brachiocephalic artery BA and coronary arteries CA, with distal end 224 of arterial return cannula 222 extending distally of balloon 232 to maintain flow of oxygenated blood into the arterial system. The compliance of balloon 232 allows it to conform around the shaft of the arterial return cannula to fully occlude the ascending aorta. Should cardioplegia catheter 230 need to be removed, balloon 232 is simply deflated and the catheter is retracted from sheath 212, with arterial return maintained by arterial return cannula 222.

While the above is a complete description of the preferred embodiments of the invention, various alternatives, modifications, substitutions and equivalents may be used without departing from the scope of the invention, which is defined by the appended claims.

What is claimed is:

1. A method of inducing cardioplegic arrest comprising:
   forming a penetration in a wall of a left chamber of the heart; positioning a cardioplegia catheter through the penetration into the left chamber of the heart;
   forming a seal between the wall of the heart and the cardioplegia catheter to inhibit leakage of blood through the penetration;
   advancing a distal end of the cardioplegia catheter in the direction of blood flow from the left chamber of the heart, through the aortic valve and into the ascending aorta;
   expanding an occlusion member on the cardioplegia catheter so as to occlude the ascending aorta downstream of the coronary ostia and upstream of the brachiocephalic artery;
   delivering cardioplegic fluid through the coronary vasculature to the myocardium so as to arrest cardiac function; and
   circulating oxygenated blood in the patients arterial system downstream of the occlusion member.

2. The method of claim 1 wherein the step of circulating comprises positioning an arterial cannula in an arterial location downstream of the occlusion member, the arterial cannula being independently positionable relative to the occlusion member.

3. The method of claim 2 wherein the arterial cannula is positioned in a peripheral artery selected from a femoral artery, iliac artery, subclavian artery or axillary artery.

4. The method of claim 3 wherein the arterial cannula is transluminally positioned from the peripheral artery to an arterial location proximate the aortic arch.

5. The method of claim 1 wherein the step of sealing comprises placing a purse string suture in the wall of the heart around the penetration.

6. The method of claim 1 wherein the step of positioning comprises placing the cardioplegia catheter in a left atrium of the heart, the step of advancing comprising advancing the cardioplegia catheter through the mitral valve, left ventricle and aortic valve into the ascending aorta.

7. The method of claim 1 wherein the step of advancing comprises sliding the cardioplegia catheter over a guiding device positioned in the left chamber of the heart and extending into the ascending aorta.

8. The method of claim 1 wherein the patient's sternum remains substantially intact during each of said steps.

9. The method of claim 1 wherein the cardioplegia catheter is positioned into the patient's chest through an access device positioned between two ribs.

10. The method of claim 9 wherein the access device comprises a body positionable between the ribs having sufficient rigidity to retract adjacent tissue and having a central opening through which the cardioplegia catheter is positioned.

11. The method of claim 8 further comprising visualizing the heart during at least a portion of said steps by means of a scope positioned in the chest.

* * * * *